(12) United States Patent
Watanabe et al.

(10) Patent No.: US 7,277,798 B2
(45) Date of Patent: Oct. 2, 2007

(54) METHODS FOR EXTRACTING SIMILAR EXPRESSION PATTERNS AND RELATED BIOPOLYMERS

(75) Inventors: Tsunehiko Watanabe, Kanagawa (JP); Yasuyuki Nozaki, Kanagawa (JP); Ryo Nakashige, Kanagawa (JP); Takuro Tamura, Kanagawa (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 0 days.

(21) Appl. No.: 09/739,525

(22) Filed: Dec. 14, 2000

(65) Prior Publication Data

US 2001/0016318 A1 Aug. 23, 2001

(30) Foreign Application Priority Data

Dec. 27, 1999 (JP) .................. 11/371434

(51) Int. Cl.
*C12Q 1/00* (2006.01)
*C12Q 1/68* (2006.01)
*G01N 31/00* (2006.01)
*G06G 7/48* (2006.01)

(52) U.S. Cl. .................. 702/19; 435/4; 435/6; 702/27; 703/11

(58) Field of Classification Search .................. 702/19
See application file for complete search history.

(56) References Cited

U.S. PATENT DOCUMENTS

| | | | | |
|---|---|---|---|---|
| 4,852,183 | A | * | 7/1989 | Abe et al. .................. 382/218 |
| 5,732,394 | A | | 3/1998 | Nakadai et al. |
| 6,069,701 | A | | 5/2000 | Hashimoto et al. |
| 6,692,916 | B2 | * | 2/2004 | Bevilacqua et al. ........... 435/6 |

FOREIGN PATENT DOCUMENTS

| | | |
|---|---|---|
| EP | 1 037 158 | 9/2000 |
| JP | 9068994 | 3/1996 |
| JP | 10-160419 | 12/1996 |
| WO | WO 00/24936 | 5/2000 |

OTHER PUBLICATIONS

Michaels et al. "Cluster Analysis and Data Visualization of Large-Scale Gene Expression Data" Pacific Symposium on Biocomputing (1998) vol. 3, pp. 42-53.*

Shimomura et al. "Differential Expression of Exons 1a and 1c in mRNAs for Sterol Regulatory Element Binding Protein-1 in Human and Mouse organs and Cultured Cells" J. Clin. Invest. (1997) vol. 99, pp. 838-845.*

Tamayo, P. et al., "Interpreting patterns of gene expression with self-organizing maps: Methods and application to hematopoietic differentiation," Proc. Natl. Acad. Sci. USA, vol. 96 (1999).

Ewing, R.M., et al., "*Large-Scale Statistical Analyses of Rice ESTs Reveal Correlated Patterns of Gene Expression,*" Genome Research, vol. 9 (1999) pp. 950-959.

van Steensel, M. AM. et al., "*Probing the Gene expression Database for candidate genes,*" European Journal of Human Genetics, vol. 7 (1999). pp. 910-919.

Alon, U. et al., "*Broad patterns of gene expression revealed by clustering analysis of tumor and normal colon tissues probed by oligonucleotide arrays,* " Proc. Natl. Acad. Sci. USA, vol. 96, (1999) pp. 6745-6750.

Heyer, L.J. et al., "*Exploring Expression Data: Identification and Analysis of Coexpressed Genes,*" Genome Research, Cold Spring Harbor Laboratory Press, US, vol. 9, No. 11, (1999) pp. 1106-1115.

Eisen, M. B. et al., "*Cluster analysis and display of genome-wide expression patterns,*" Proc. Natl. Acad. Sci, USA, vol. 95 (1998) pp. 14863-14868.

"Estimation of Gene Functions", Experimental Medicine (Sep. 1990), vol. 17, No. 13, pp. 1670-1673, and 1692, (English abstract only).

* cited by examiner

*Primary Examiner*—Ram R. Shukla
*Assistant Examiner*—Eric S DeJong
(74) *Attorney, Agent, or Firm*—Reed Smith LLP; Stanley P. Fisher, Esq.; Juan Carlos A. Marquez, Esq.

(57) ABSTRACT

The present invention provides methods for extracting similar expression patterns and related biopolymers considering natures that are characteristic of expression data of, for example, genes. A segment of experiment cases which includes an expression of interest is selected as a search range among an expression pattern of a reference gene or the like. By comparing the selected segment of the expression pattern with expression patterns of a group of candidate genes or the like, genes having an expression pattern with at least a partial similarity are searched from the group of candidate genes. A partially taken out curve (a part of an, expression pattern) is transferred to overlap an expression pattern curve of a candidate gene to search expression patterns with a similar pattern shape.

14 Claims, 24 Drawing Sheets

Fig.12

Reference gene

|  | 1 | 2 | .... | case_num |
|---|---|---|---|---|
| Target[] | 3 | 5 |  |  |

Fig. 15A Gene expression pattern
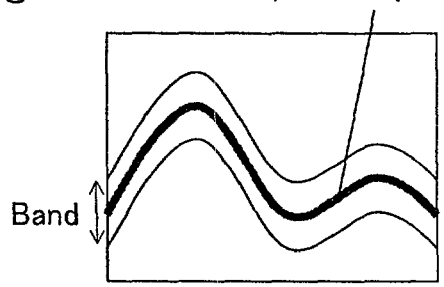
Fig. 15D Gene expression pattern
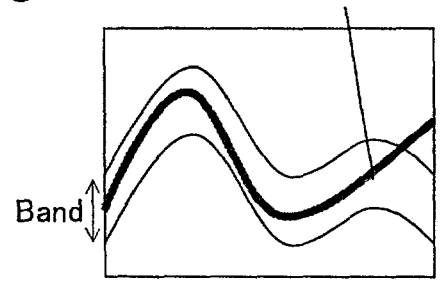
Fig. 15B Gene expression pattern
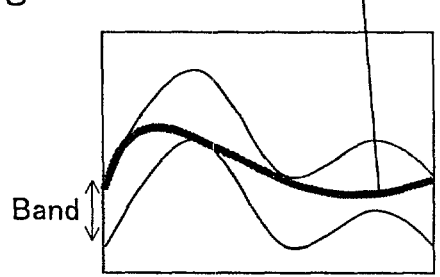
Fig. 15E Gene expression pattern
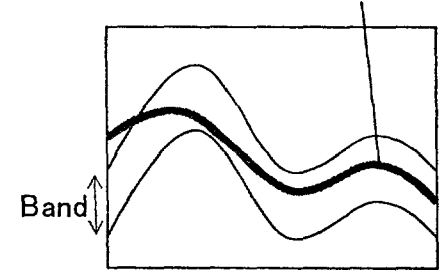
Fig. 15C Gene expression pattern
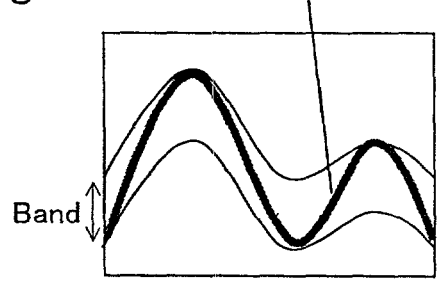
Fig. 15F Gene expression pattern
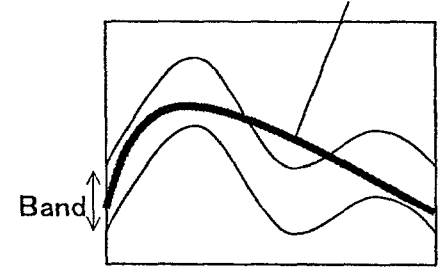

Segment is fixed along the horizontal axis

Fig. 18

| Similarity | Name of gene | Search segment | Detailed information of gene |
|---|---|---|---|
|  |  | 10  15 | Mus musculus mitochondrial ATP synthase coupling factor 6 mRNA, nuclear gene encoding mitochondrial protein, complete cds. |
| : | : | 10  15 | Mus musculus clone UWGC:mbac82 from 14D1-D2 (T-Cell Receptor Alpha Locus), complete sequence. |
| : | : | 10  15 | Mus musculus platelet-activating factor acetylhydrolase isoform Ib gamma subunit (PAF-AH gamma) mRNA, complete cds. |
|  |  | 10  15 | Mouse complete gene for a mouse kallikrein (serine protease) and fragment of a second kallikrein gene. Genes are mGK-1 (complete gene) and mGK-2 (fragment). Kallikreins are necessary for the processin |

Fig. 19A  Gene expression data
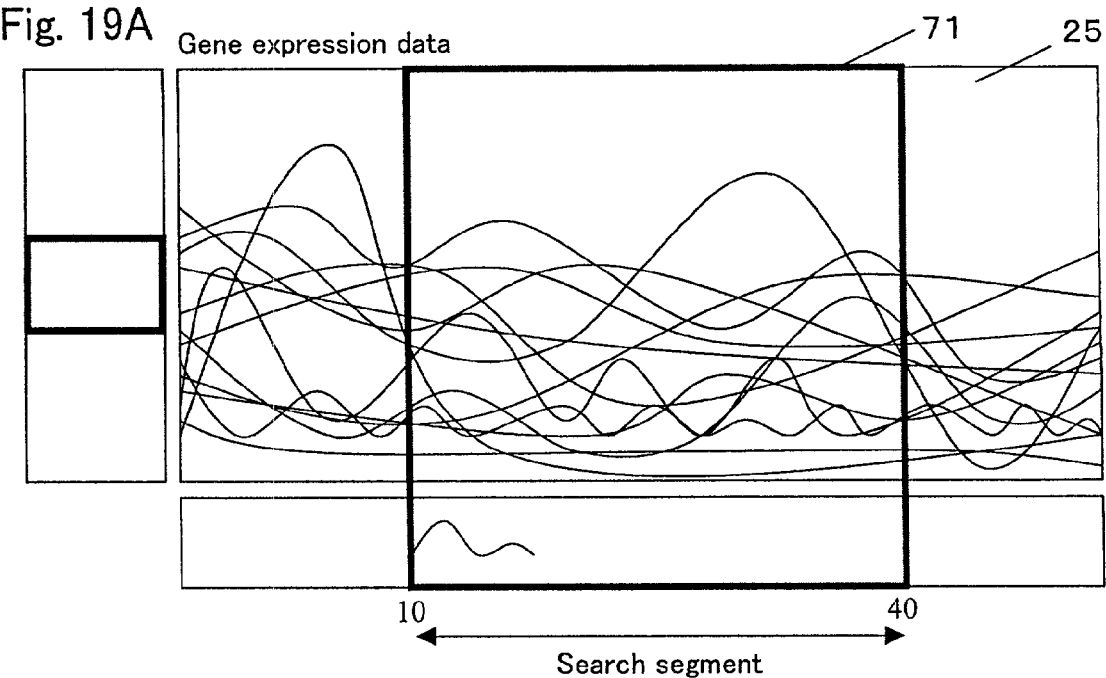
10                      40
Search segment
Fig. 19B
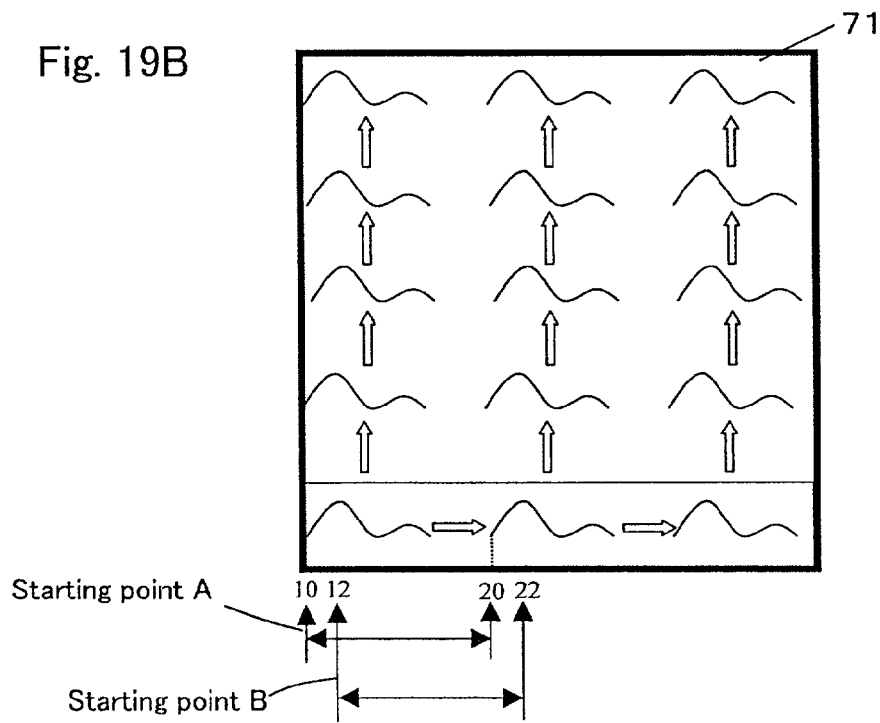
Starting point A    10 12      20 22
Starting point B Starting point of search
Search segment

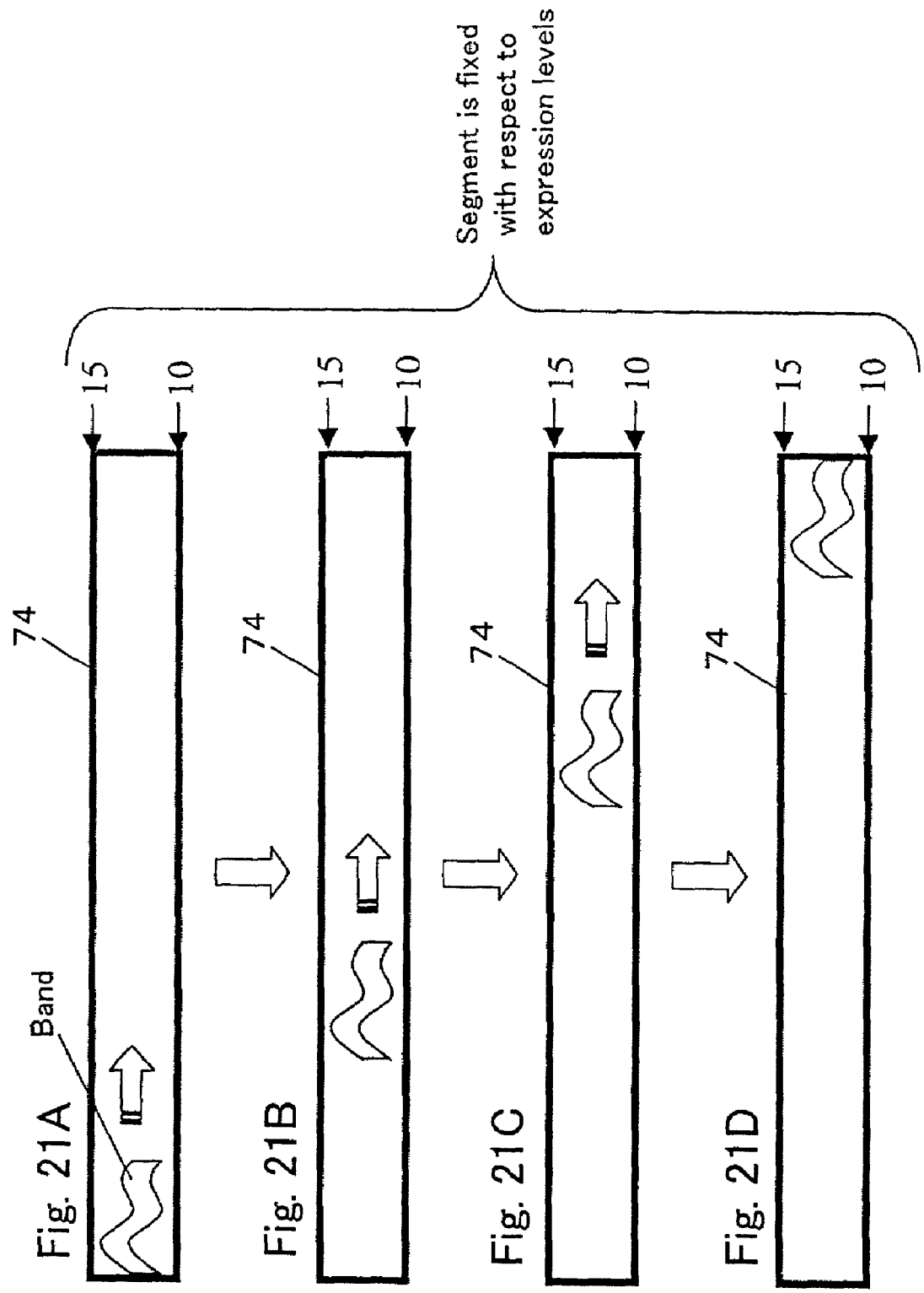

A group of numerous candidate genes

The entire gene expression pattern is the target of the search

Gene searched by conventional method

METHODS FOR EXTRACTING SIMILAR EXPRESSION PATTERNS AND RELATED BIOPOLYMERS

The present application claims the benefit of priority under 35 U.S.C. §119 of Japan Patent Application No. 371434/1999, filed Dec. 27, 1999. This application is explicitly incorporated herein by reference in its entirety and for all purposes.

FIELD OF THE INVENTION

The present invention relates to a method for extracting from a group of numerous biopolymers a biopolymer which is relative to a certain biopolymer such as a gene with respect to its expression.

BACKGROUND OF THE INVENTION

With the increase in the number of species that have been determined of their genome sequences, so called genome comparison has extensively been performed. Genome comparison aims at finding new facts based on gene difference among species, for example, finding genes involved in evolution, finding a collection of genes which are considered to be common to all species, or, conversely, studying the nature unique to specific species.

The recent development of infrastructures such as DNA chips and DNA microarrays has changed the interest in the art of molecular biology from information of interspecies to information of intraspecies, namely coexpression analysis, and broadened the study covering from extraction of information to correlation of information, including the conventional comparison between species.

For example, if an unknown gene has an expression pattern identical to that of a known gene, the unknown gene can be assumed to have a similar function to that of the known gene. Such functional meanings of genes and proteins are studied as function units or function groups. The interactions between the function units or function groups are also analyzed by correlating with known enzymatic reaction data or metabolism data, or more directly, by knocking out or overreacting a specific gene to eliminate or accelerate expression of genes to study the direct and indirect influences on gene expression patterns of a whole collection of genes.

Herein, an expression pattern of a gene is represented as a curve (or a line graph) of successive expression levels obtained from a series of experiment cases performed on the gene, where the horizontal and vertical axes represent experiment cases and expression levels, respectively. The expression pattern is not limited to an expression pattern of a gene but may be an expression pattern of other biopolymer such as DNA, cDNA, RNA, a DNA fragment or a protein. Herein, expression patterns of genes are exemplified for describing the present invention. Specific examples of the experiment cases along the horizontal axis include experiments in a time course, body parts of an organism, species, parts of a nucleotide sequence, and genes.

One exemplary analysis of expression patterns where experiments in a time course are taken as the horizontal axis, is the expression analysis of yeast by the group of P. Brown et al. from the Stanford University (Michel B. Eisen et al., Cluster analysis and display of genome-wide expression patterns, *Proc. Natl. Acad. Sci.* (1998), December 8; 95(25): 14863-8). They used a gene called cdc6 mutant strain to obtain expression data of the gene upon experiments in a time course. The expression data include a time sequential expression pattern obtained with centrifugation, a time sequential expression pattern during the budding period, a time sequential expression pattern obtained with a shock by high temperature, a time sequential expression pattern obtained with a shock by low temperature and a time sequential expression pattern obtained with the diauxic shift method. These expression data are combined to cluster the expression patterns, thereby succeeding in specifying the function of the gene.

According to one method for analyzing gene expressions, genes having similar patterns to that of a selected gene (a reference gene) shown in FIG. 24B are extracted from expression patterns of a group of numerous genes (candidate genes) shown in FIG. 24A. The extracted genes can be potential members of a function group or a function unit to which the reference gene belongs to.

FIGS. 24C and 24D schematically show the searching process and the results thereof according to this conventional method, respectively. According to this conventional method, genes having expression patterns similar to the expression pattern of the reference gene along their entire patterns are extracted. Specifically, an expression pattern of each gene is taken as a single vector (a vector having expression levels as components of independent axes representing multiple experiment cases in a multidimensional space). Then, the vectors are compared to give similarity (or dissimilarity) of the genes. Alternatively, genes can be extracted based on curve data (expression pattern data) selected by a user instead of actual gene data. The expression level along the vertical axis represents the proportion of the number of amplified genes. Actual measurement values depend on the experiment process, and the index of the expression levels may be, for example, fluorescent intensities from fluorescent labels labeling genes hybridized on a DNA chip, chemiluminescent intensities from chemiluminescent labels, values obtained by detecting, with an electrode, electric signals induced by chemical reactions of genes attached on a DNA chip, or mass spectrographic values obtained by measuring the time of flight of gasified hybridized genes.

According to such conventional method, however, genes to be extracted are only those having similar expression patterns along the entire expression pattern (i.e., for all experiment cases) of the selected reference gene.

For example, the conventional method is not capable of recognizing an expression pattern similar to that of the reference gene when the expression pattern data of the candidate gene contains a measurement error as shown in FIG. 22A which is caused by a difference between experimental environments. Moreover, when a plurality of genes have similar expression patterns for having similar functions in a part of the segment of the time course (for a part of consecutive experiment cases) but have different expression patterns for having different functions in another segment, curves are similar in a particular segment as shown in FIG. 22B. According to the conventional method, such a group of curves having similar curves in a particular segment cannot be extracted.

An expression regulatory effect of genes consists of a series of cascades where expression of one gene induces or inhibits expression of another gene. The term "cascades" as used herein refers to chain expressions of multiple genes as schematically shown in FIG. 23 where gene 1 induces expression of gene 2, gene 2 in turn induces expression of gene 3, and gene 3 in turn induces expression of gene 4. A further complicated network is formed by a combination of such cascades. In such gene cascades, the peaks of expressions of multiple genes are ranged along the time axis while their expression patterns have very similar shapes. FIG. 22D also shows a part of such cascades. This gene cascades cannot be detected by the conventional method.

In addition, the conventional method cannot detect, for example, a gene expression pattern shown in FIG. 22E where the expression of the gene is repressed, a gene expression pattern shown in FIG. 22C where the expression of the candidate gene has the same pattern as the expression of the reference gene but with a large and constant difference, and a gene expression pattern shown in FIG. 22F where the expression of the candidate gene has the same pattern as the expression of the reference gene but is stretched under a constant magnification.

SUMMARY OF THE INVENTION

In order to solve such conventional problems, the present invention has an objective of providing methods for extracting similar expression patterns and related biopolymers considering properties characteristic of expression data such as gene expressions. Particularly, the present invention has an objective of providing methods for extracting similar expression patterns and related biopolymers which can aid: an analysis where candidate expression patterns contain a measurement error; an analysis where a plurality of biopolymers (e.g., genes) have similar expression patterns for having similar functions in a part of the segment of the time course but have different expression patterns for having different functions in other segments; or an analysis of gene cascades.

According to the present invention, a segment of experiment cases including the expression of interest is first selected by a user as a search range among the entire expression pattern of a reference gene or the like as shown in FIGS. 2A and 2B. The selected segment of expression pattern is compared with an expression pattern of, for example, a candidate gene as shown in FIG. 2C to search for a gene or the like having an expression pattern with at least a partial similarity to that of the reference gene. By using this technique, similar genes or the like can be extracted for the case of FIG. 22A by leaving out the error range from the search segment, and for the case of FIG. 22B by including in the search segment only the range showing similar expression patterns.

The curve (the expression pattern) can partially be taken out and transferred in directions along vertical axis (axis of expression levels) and horizontal axis (axis of experiment cases) as shown in FIG. 2D to overlap the expression pattern of the candidate gene as shown in FIG. 2E, thereby finding an expression pattern with a similar shape. Furthermore, the partially-taken-out curve (expression pattern) can be processed to search for a wider range of gene curves with similar patterns. For example, the taken-out curve may be inverted up-side-down to search for a repressive gene, or the taken-out curve may be stretched or shrunk in the vertical direction to search for an expression pattern under a constant magnification.

The shape of the selected part of the expression pattern of the reference gene or the like and a corresponding part of the expression pattern of the candidate gene or the like can be compared by the following techniques. (i) a technique in which a band is formed by providing a predetermined width to the selected expression pattern of the reference gene or the like to extract genes having expression patterns that fall within this band from the group of candidate genes; (ii) a technique in which similarity between a reference gene or the like and a candidate genes or the like is calculated; or (iii) a combination of techniques (i) and (ii) where the similarity between expression patterns of genes or the like which fall within the band is calculated.

The invention relates to a method for extracting an expression pattern similar to a reference expression pattern, from a collection of candidate expression patterns that represent relationships between multiple experiment cases and expression levels of the biopolymers, the method comprising the steps of taking out a part of the reference expression pattern, and extracting from the candidate expression patterns an expression pattern including a pattern shape similar to the pattern shape of the taken-out expression pattern.

The taken-out pattern may be processed, and then an expression pattern including a pattern shape similar to the pattern shape of the processed pattern may be extracted from the candidate expression patterns. Effective processing includes inverting the taken-out pattern shape up-side-down with respect to a vertical axis (an expression level axis), and altering magnification of the taken-out pattern in the direction along the vertical (expression levels) or horizontal (experiment cases) axis.

Similarity of the pattern shapes are judged by forming a band-shape pattern having a constant width in the direction along the vertical axis (expression level axis) by adding and subtracting a predetermined value to/from the expression levels for every experiment cases within the taken-out pattern of the reference expression pattern or within the processed taken-out pattern, and then extracting from the candidate expression patterns an expression pattern including a part that entirely falls within the band-shape pattern.

An expression pattern including a part that entirely falls within the band-shape pattern is extracted while transferring the band pattern in the vertical and/or horizontal direction.

The biopolymers to which the method for extracting similar expression patterns are applied are genes, DNAs, cDNAs, RNAs, DNA fragments or proteins. The experiment cases are experiments in a time course, different species, different parts of body, presence/absence of an artificial condition, or a combination among any of the above.

The present invention also relates to a method for extracting a biopolymer relative to a reference biopolymer with respect to their expressions, from candidate biopolymers by comparing expression patterns that represent relationships between multiple experiment cases and expression levels of biopolymers, the method comprising the steps of taking out a part of the expression pattern of the reference biopolymer, and extracting from the candidate biopolymers a biopolymer having an expression pattern including a pattern shape similar to the pattern shape of the taken-out expression pattern.

The taken-out pattern may be processed, and a biopolymer having an expression pattern including a pattern shape similar to the pattern shape of the processed pattern may be extracted from the candidate biopolymers. Effective processing includes inverting the taken-out pattern shape upside-down with respect to a vertical axis (an expression level axis), and altering magnification of the taken-out pattern in the direction along the vertical (expression levels) or horizontal (experiment cases) axis.

Similarity of the pattern shapes are judged by forming a band-shape pattern having a constant width in the direction along the vertical axis (expression level axis) by adding and subtracting a predetermined value to/from the expression levels for every experiment cases within the taken-out pattern, and extracting from the candidate biopolymers a biopolymer having an expression pattern including a part that entirely falls within the band-shape pattern.

A biopolymer having an expression pattern including a part that entirely falls within the band-shape pattern is extracted while transferring the band pattern in the vertical and/or horizontal direction.

The biopolymers to which the method for extracting a related biopolymer is applied are genes, DNAs, cDNAs, RNAs, DNA fragments or proteins.

The biopolymers to which the method for extracting similar expression patterns are applied are genes, DNAs, cDNAs, RNAs, DNA fragments or proteins. The experiment cases are experiments in a time course, different species, different parts of body, presence/absence of an artificial condition, or a combination among any of the above.

This specification includes part or all of the contents as disclosed in the specification and/or drawings of Japanese Patent Application No. 11-371434, which is a priority document of the present invention.

BRIEF DESCRIPTION OF THE DRAWINGS

FIG. 12 is a diagram showing an exemplary expression pattern data of a reference gene.

FIGS. 15A to 15F are diagrams for illustrating exemplary patterns that are recognized or not recognized as similar patterns.

FIG. 18 is a view showing an exemplary display of gene data in the order of similarity.

FIGS. 19A and 19B are diagrams showing an example of automatic searching within a designated search segment.

FIGS. 21A to 21D are diagrams for illustrating the sliding movement of a band within the selected segment frame in the direction along the horizontal axis.

DESCRIPTION OF THE PREFERRED EMBODIMENTS

Figure 1:
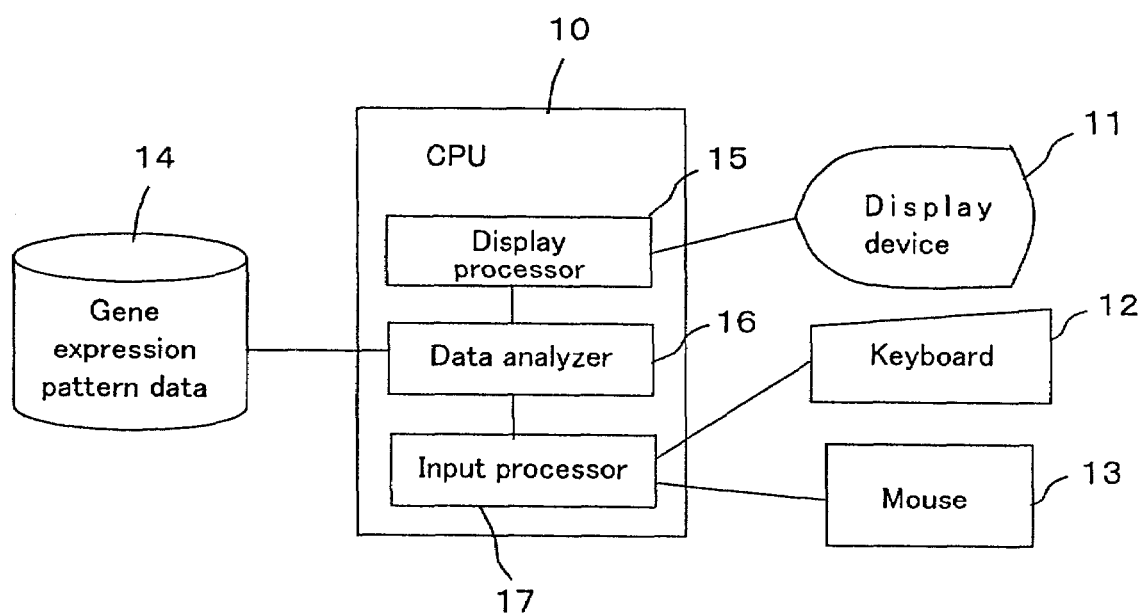
FIG. 1 is a schematic view showing an example of a system configuration according to the invention.
Figure 2A:
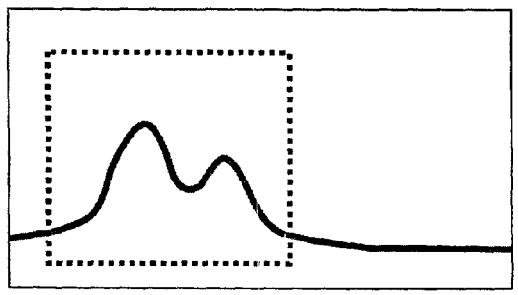
FIGS. 2A to 2E are diagrams for showing an example of searching for a similar pattern according to the invention.
Figure 2B:
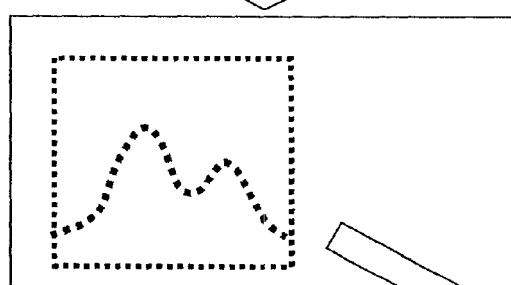
Figure 2D:
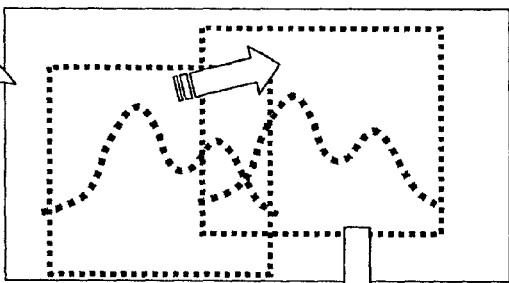
Figure 2C:
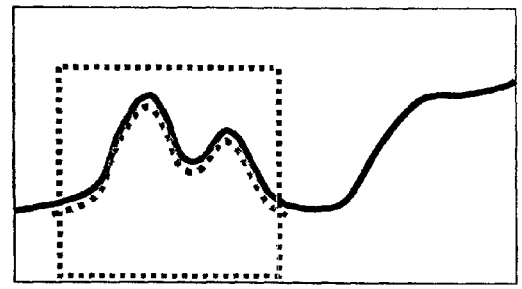
Figure 2E:
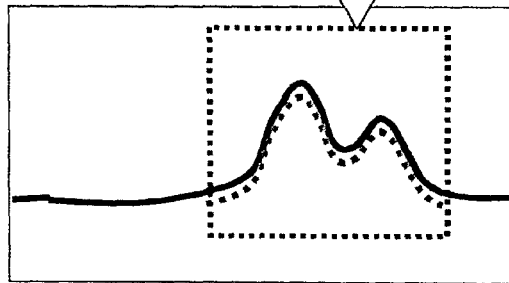

Hereinafter, the present invention will be described in more detail with reference to the accompanying drawings. For clearer understanding, graphs of expression patterns exemplified in the following examples have the horizontal and vertical axes representing experiment cases in a time course and gene expression levels, respectively. It should be appreciated that the present invention is not limited to expression patterns of genes or to expression patterns where the horizontal axis represents experiment cases in a time course.

For example, when expression and expression levels of a gene which acts upon development of frogs are to be studied, first, a mass amount of frog eggs are simultaneously fertilized and thereafter the presence/absence of copies of that gene can be checked or the number of copies of the gene can be counted with the lapse of time. According to the present invention, in such an experiment, states of the eggs are observed with the lapse of time, and every measurement of the expression/expression level of the gene from the fertilized egg is considered as one experiment case (consequently, resulting in experiment cases in a time course). Alternatively, the experiment cases may be such that the comparison is made, for example, by the difference between experimental environments (e.g., presence/absence of stimulation by heat, or before/after administration of a drug), by the difference between time points during a cell cycle (e.g., a time point of cell division, or a time point when a nutrient is given), by the difference between parts of body, and by the difference between species.

As one example of experiment cases other than those in a time course, the horizontal axis may represent parts of body. Specifically, the horizontal axis may represent parts of body such as brain, heart, kidney and the like. The plotted expression levels of a gene, DNA, cDNA, RNA, a DNA fragment, a protein and the like from each of the parts can be joined to obtain an expression pattern. The present invention is applicable to such a case. The present invention is also applicable to expression patterns of genes, DNAs, cDNAs, RNAs, DNA fragments, proteins and the like, where the horizontal axis represents different species such as mammals (e.g., human and mouse), reptiles, amphibia and the like, to find the difference between species. Furthermore, the present invention is applicable to expression patterns where the horizontal axis represents presence/absence of external influences such as injection, heat shock, nutrition supply and the like to different species or different parts of body, or generally to expression patterns where the horizontal axis represents a combination of selected parts of body, species and experiments in a time course.

When intracellular activity such as cell division and energy yield is caused in an organism such as yeast or human, some nuclear genes of a cell are copied which results in protein production. Briefly, the cell starts to function. Such function is referred to as "gene expression" and the number of copied genes is referred to as an "expression level". By observing expression levels of genes under different experiment cases, it can be appreciated that an increase/decrease in the expression levels change depending on the functions of the genes. Herein, such changes are referred to as "expression patterns". Instead of genes, amounts of DNAs, cDNAs, RNAs, DNA fragments or proteins may also be measured.

FIG. 1 is a schematic view showing an example of a system configuration employed for the present invention. The system is provided with gene expression pattern data 14 for storing numerated gene expressions levels in a series of cell process, a data analyzer 16 for fetching and analyzing desired information from the expression pattern data 14, a display processor 15 for visualizing and displaying the results, a display device 11 on which the results are actually displayed, pointing devices such as a keyboard 12 and a mouse 13 for entering values into the system and for selection, and an input processor 17 for transmitting such commands to the data analyzer 16. The display processor 15, the data analyzer 16 and the input processor 17 are provided on a central processing unit 10. The central processing unit 10 is realized with a computer and a program thereof.

Figure 3:
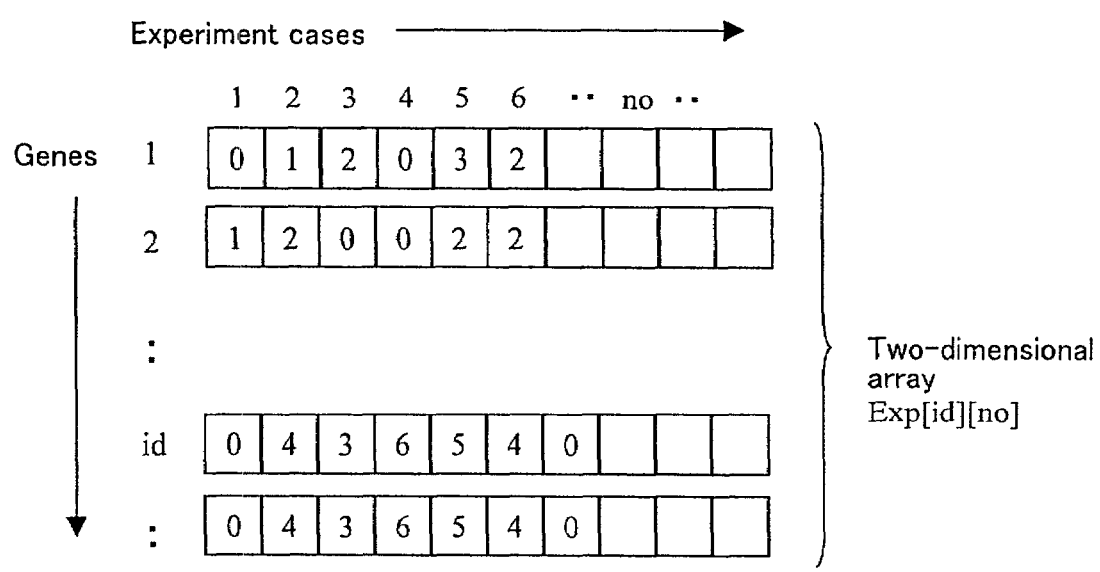
FIG. 3 is a schematic view showing an exemplary expression pattern data of candidate genes.

FIG. 3 is a schematic view showing a specific structure of expression pattern data of candidate genes stored in the gene expression pattern data 14. The expression data of a group of candidate genes is represented as a two-dimensional array Exp[ ] [ ]. Specifically, numerated expression level data of a gene corresponding to gene ID (id) under an experiment case (no) is stored as Exp[id] [no].

Figure 4:
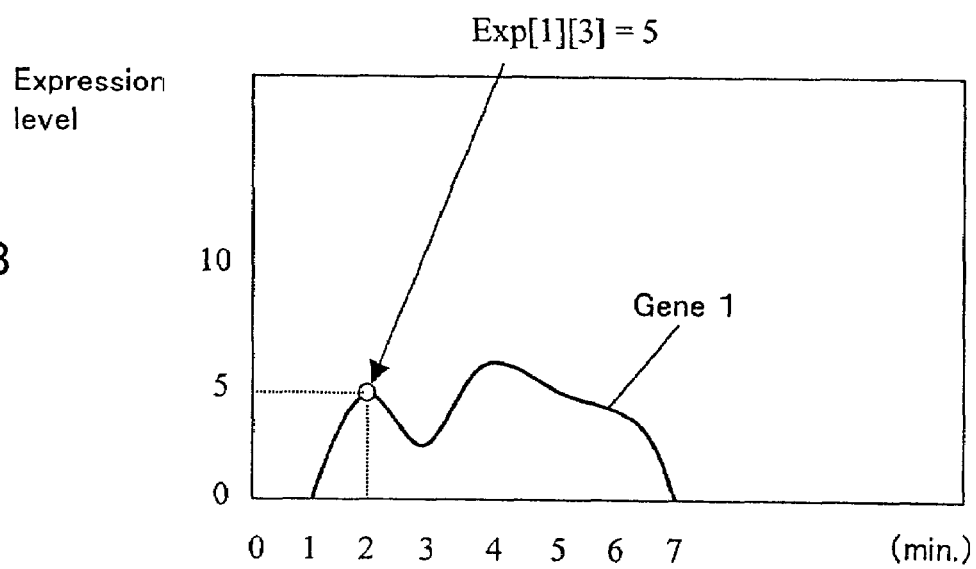
FIGS. 4A and 4B are schematic views for illustrating expression pattern data of an exemplary gene in a two-dimensional array and a corresponding expression pattern data of the same gene drawn as a graph based on this data.

FIGS. 4A and 4B are schematic views for illustrating expression pattern data of an exemplary gene and a corresponding expression pattern of the same gene drawn based on this data. The experiment cases are in a time course. For example, the expression pattern data may be obtained by performing hybridization reaction to samples collected with the lapse of time using the same type of DNA chips.

FIG. 4A shows expression pattern data of a gene 1 and FIG. 4B shows an expression pattern of the gene 1 represented as a graph. The horizontal axis of the graph represents a time course (min.) while the vertical axis represents expression levels (unit undetermined). The curve (the line graph) shown in FIG. 4B correlates with the array Exp[ ] [ ] in FIG. 4A. When this curve is to be represented as two-dimensional array Exp[ ] [ ], Gene ID "1" and the order of the experiment case are made to substitute for the first and second subscripts, respectively. The values of this array indicate the expression levels of this gene. According to this example, data of expression level of Gene 1 after i minutes can be represented as Exp[1] [i+1]. For example, data after 2 minutes where the expression level is 5 corresponds to the third experiment case. Accordingly, this data can be represented as array Exp[1] [3]=5.

Figure 5:
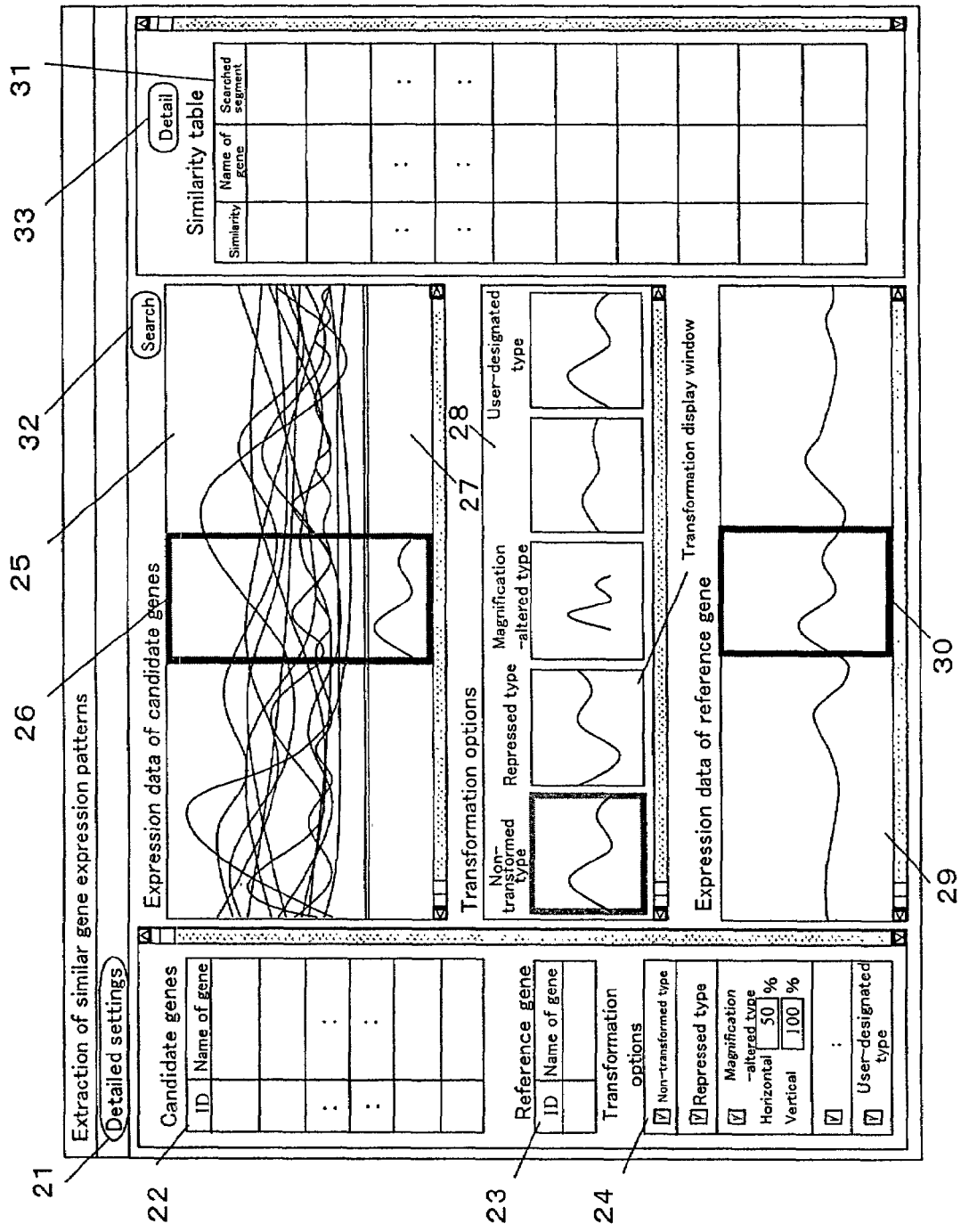
FIG. 5 is a view for illustrating an exemplary display screen of a display device.

FIG. 5 is a view for illustrating an exemplary display screen of the display device 11 of the system shown in FIG. 1. The display screen includes: a candidate genes displaying box 22 where data of the candidate genes are entered and where attributes of the genes are displayed; a graph display region 25 for the candidate genes, where the gene expression patterns of multiple genes entered in the candidate genes displaying box 22 are displayed together; a reference gene displaying box 23 where data of a reference gene is entered and where attributes of the reference gene are displayed; and a graph display region 29 for the reference gene where the gene expression pattern of the reference gene in the reference gene displaying box 23 is displayed.

Further provided are a selected segment frame 30 for selecting a segment to be subjected to a search from the gene expression pattern displayed on the graph display region 29 for the reference gene, a transformation options box 24 for indicating types of transformations performed on the expression pattern in the selected segment frame 30, and a transformation option displaying region 28 for displaying transformed patterns according to the transformation types selected in a transformation option box 24. These transformation options will allow to efficiently find, for example, a gene expression which is involved in inhibition of other gene expression. The selected segment frame 30 can appropriately be adjusted with respect to its position and width in the horizontal direction, for example, by dragging the frame with a mouse pointer or the like. The graph display region 25 for the candidate genes is provided with a search segment frame 26 whose starting point can be set by the user, for example, by dragging with a mouse pointer or the like in the horizontal direction.

Search for genes having similar expression patterns within the selected segment frame 30 is initiated by clicking a search button 32. The results of the search will be displayed on a similarity table 31 in the order of similarity. In the figure, the similarity table 31 includes columns for similarity, name of gene and searched segment. By clicking a detail button 33 above the similarity table 31, attributes for each of the genes displayed on the table 31 will be displayed on a separate window.

Figure 6:
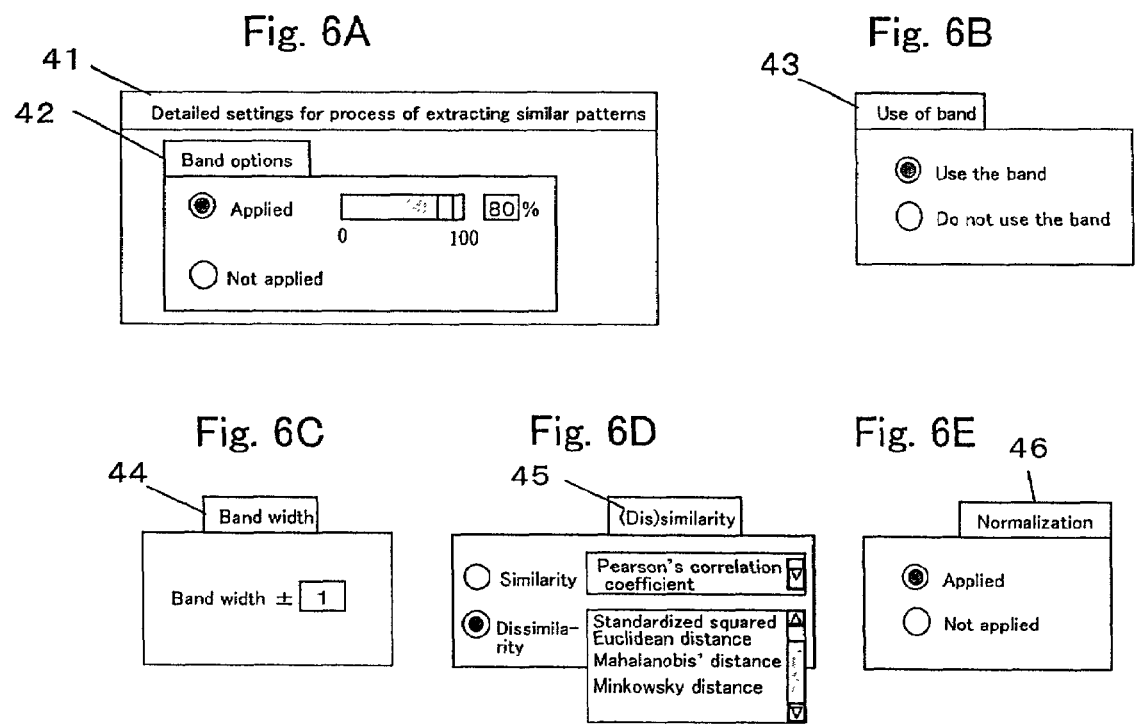
FIGS. 6A to 6E are views for illustrating a detailed setting window.

By clicking a detailed settings button 21 on the display screen, a detailed settings window 41 schematically shown in FIG. 6A will appear. The detailed settings window 41 includes a band option setting tag 42 shown in FIG. 6A for setting band options, a band use tag 43 shown in FIG. 6B for setting use of the band, a band width setting tag 44 shown in FIG. 6C for setting the width of the band used for searching for similar patterns, a similarity (dissimilarity) tag 45 shown in FIG. 6D for selecting a method for calculating similarity (dissimilarity), and a normalization tag 46 shown in FIG. 6E for setting application of normalization process to the reference gene and the candidate genes. The "band" as used herein refers to a region obtained by adding/subtracting a predetermined value to/from the values of the expression levels to give a width in a vertical direction as will be described later.

With the selected segment frame 30, the user will select a desired segment to be searched from the gene expression pattern displayed on the graph display region 29 for the reference gene (FIG. 5). Based on the curve (pattern shape) selected with the selected segment frame 30, similar curves are extracted from the gene expression patterns of the candidate genes displayed on the graph display region 25 for the candidate genes. Specifically, patterns which partially include a curve resembling the pattern shape within the selected segment frame 30 are extracted from the gene expression patterns displayed on the graph display region 25 for the candidate genes.

The user will move the search segment frame 26 to the right or left to determine the starting point of search in the graph display region 25 for the candidate genes. For example, in order to observe the state of cascades of genes in the selected search segment frame 26, the user may appropriately move the selected segment frame to find similar genes. The starting point of search can be set automatically. Alternatively, multiple starting points of search may be set automatically for automatic searches starting from sequentially-shifted starting points.

Figure 7:
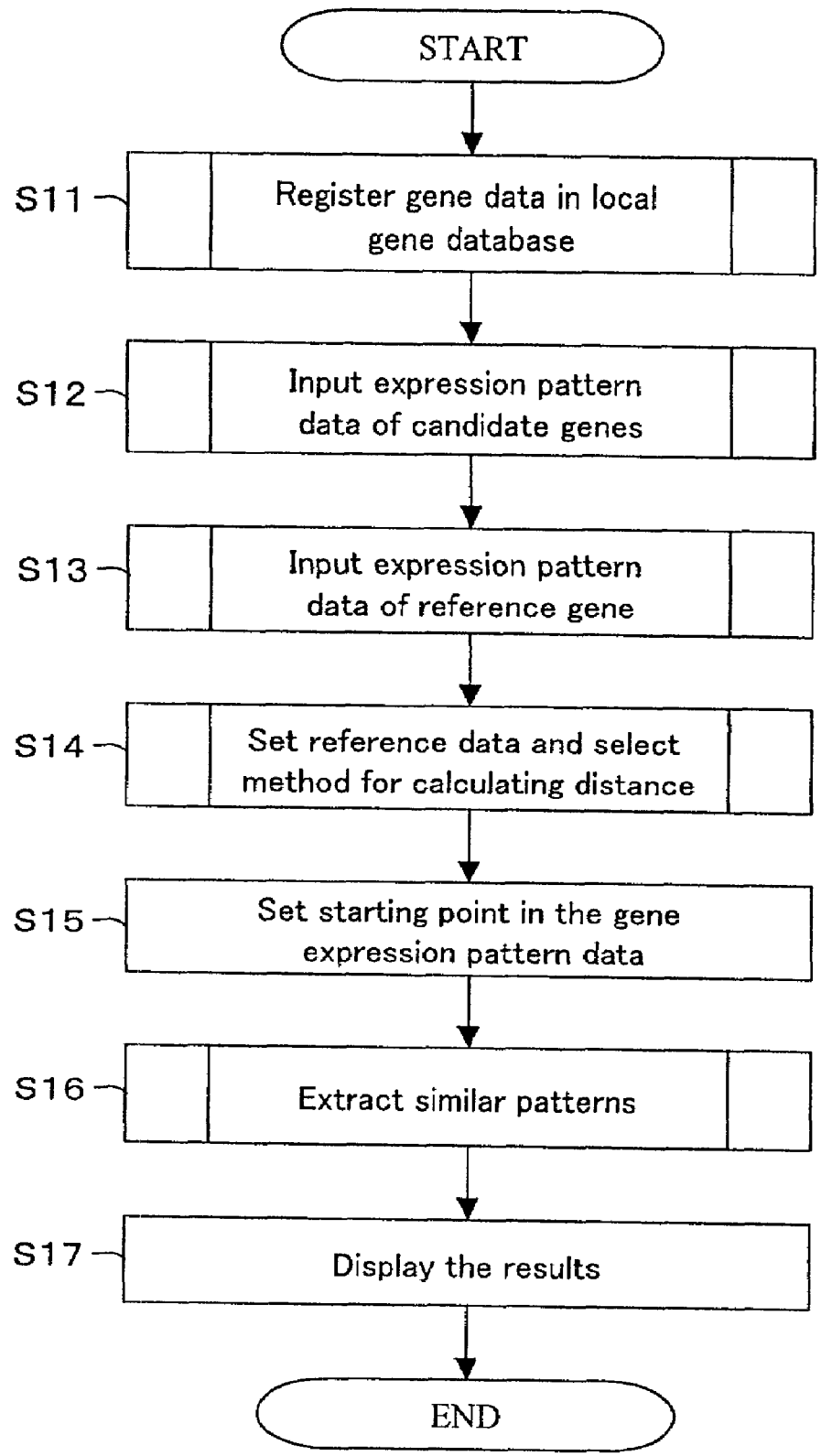
FIG. 7 is a flowchart showing a general method for extracting similar gene expression patterns according to the present invention.

FIG. 7 is a flowchart showing a general method for extracting similar gene expression patterns according to the present invention. First, data is read out from the gene expression pattern data 14 into the data analyzer 16 shown in FIG. 1 (Step 11). Specific shapes of individual gene expression patterns are such as those described above with reference to FIG. 3. Then, the user fetches expression patterns of genes to be subjected to the search as candidate genes from the gene expression pattern data in the data analyzer 16 shown in FIG. 1 (Step 12). An expression pattern of a reference gene is also fetched (Step 13). As will be described later, data generated by the user can also be entered as expression pattern data of a reference gene. Then, the user is to determine detailed settings of the expression pattern of the reference gene and to select a method for calculating a distance of similarity (dissimilarity) (Step 14).

Then, the starting point of search for genes resembling the reference gene is determined in the candidate gene expression data (Step 15). Herein, the value of the starting point is determined by the user by moving the search segment frame 26 to the right or left on the display screen (FIG. 5). This value is stored as variable Ts. Next, genes resembling the reference gene are extracted from the group of candidate genes (Step 16). Finally, the extracted candidate genes are displayed on the similarity table 31 in the order of their similarity (Step 17).

Figure 8:
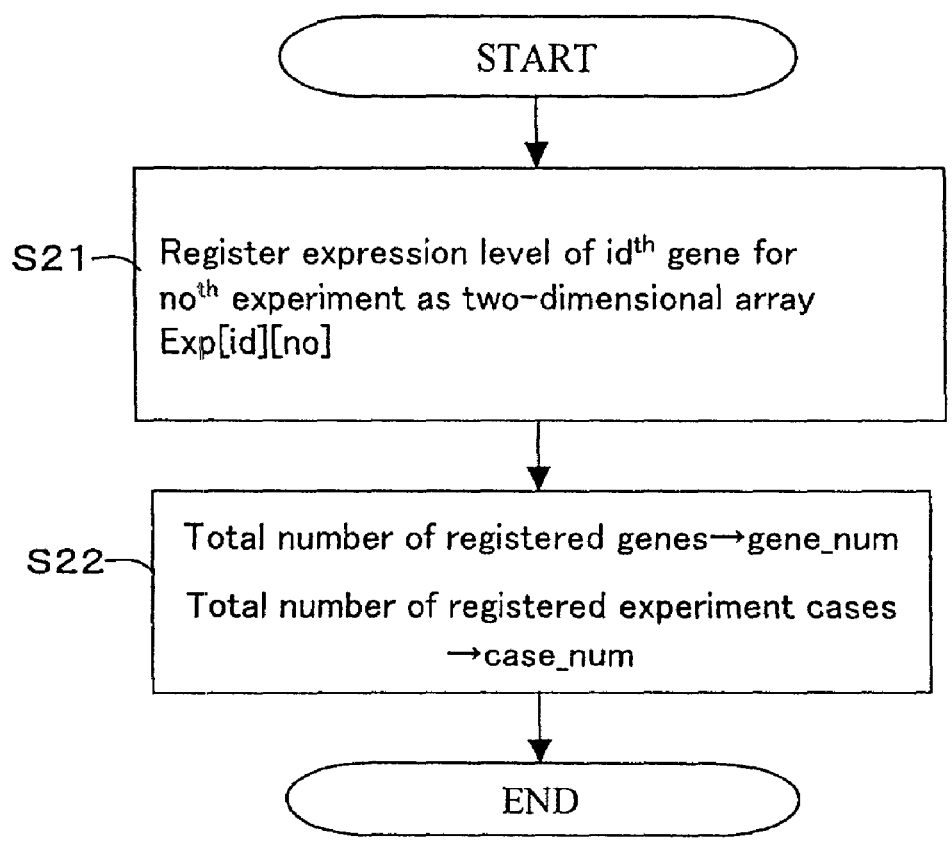
FIG. 8 is a flowchart of the process of registering candidate gene expression pattern data.

FIG. 8 is a flowchart of a detailed process of registering expression pattern data of candidate genes at Step 11 in FIG. 7.

Figure 9:
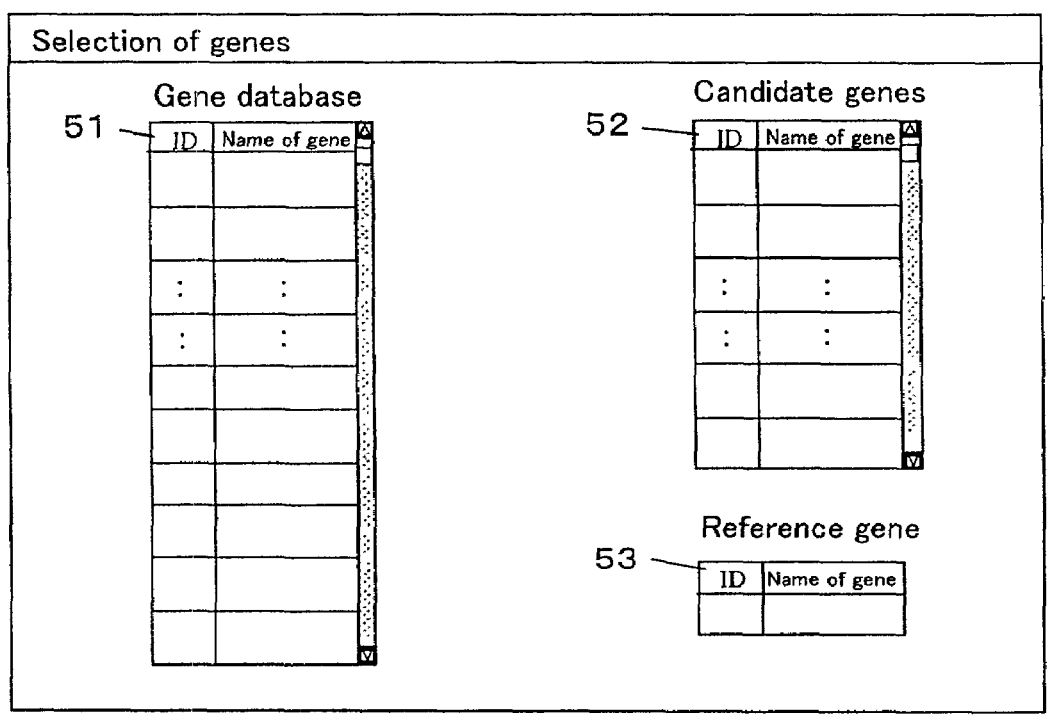
FIG. 9 is a view showing an example of selecting candidate genes and a reference gene from gene data.

First, as shown in FIG. 9, the gene expression pattern data 14 accumulated in the present system is displayed on a local gene database displaying box 51 on a separate window. The local gene database display box 51 includes gene ID and name of the stored genes. The gene data for candidate genes may be selected and stored, for example, by dragging and dropping the desired data to candidate genes displaying box 52 with a pointing device. The data in the candidate genes displaying box 52 is input into the candidate genes displaying box 22 shown in FIG. 5. Once the candidate genes are input into the candidate genes displaying box 22, gene expression patterns of candidate genes are displayed on the graph display region 25 for the candidate genes according to their expression levels. At the same time, the expression level of $id^{th}$ gene for $no^{th}$ experiment case is registered as two-dimensional array Exp[id] [no] as described with reference to FIG. 3 (Step 21). Next, the total number of the registered genes and the total number of the experiment cases are stored as variables gene_num and case_num, respectively (Step 22).

Figure 10:
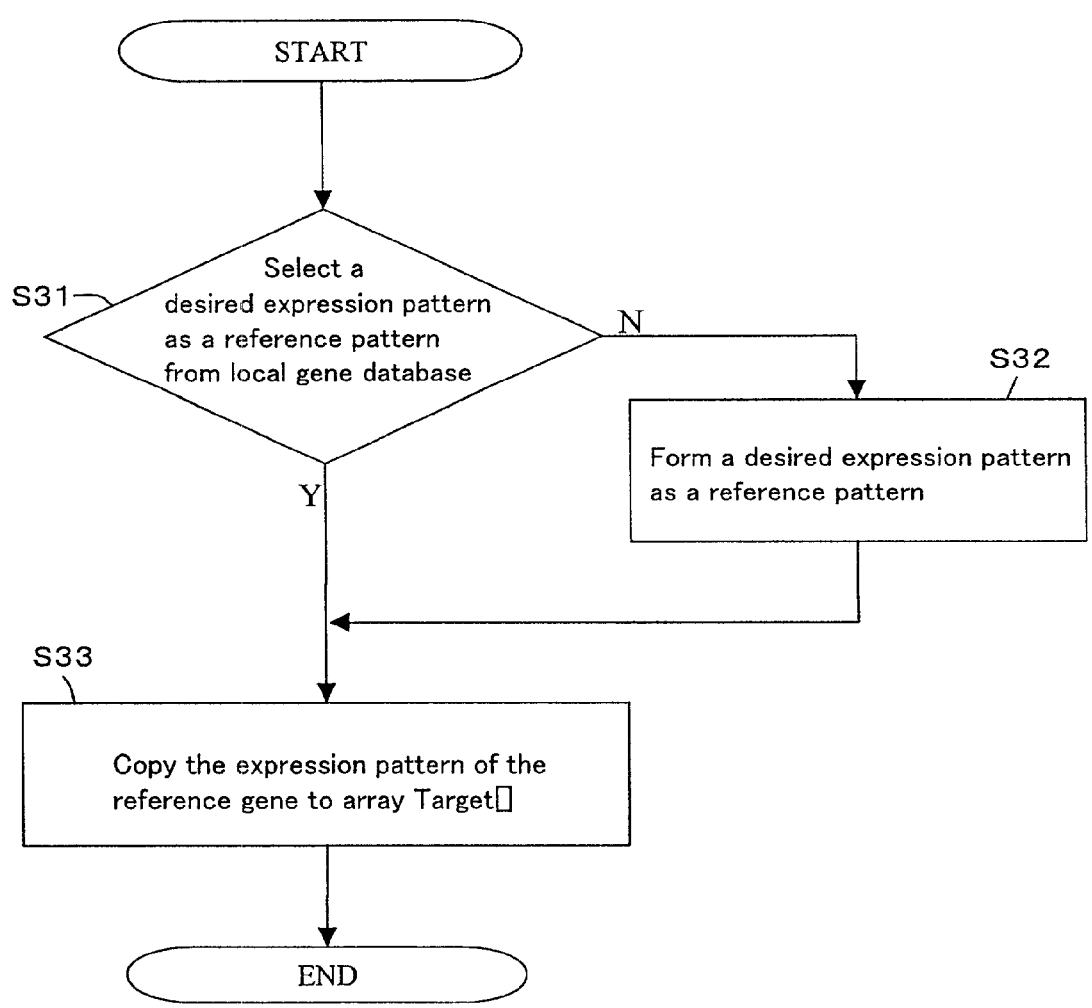
FIG. 10 is a flowchart of a process of inputting expression data of a reference gene.

FIG. 10 is a flowchart of a detailed process of entering expression pattern data of a reference gene at Step 12 in FIG. 7.

In order to select a reference gene from the local gene database, expression pattern data of a reference gene is selected from the local gene database displaying box 51 (FIG. 9) by dragging and dropping the data into a reference gene displaying box 53 with a pointing device (Step 31). The data in the reference gene displaying box 53 is input into the reference gene displaying box 23 shown in FIG. 5. Once the reference gene is input into the reference gene displaying box 23, a gene expression pattern of the reference gene is displayed on the graph display region 29 for the reference gene.

Then, the expression pattern of the reference gene is copied to array Target[ ] (Step 33). When the reference gene is not selected from the local gene database, a gene expression pattern is generated by the user and the generated gene expression pattern is copied to array Target[ ] (Step 32).

Figure 11:
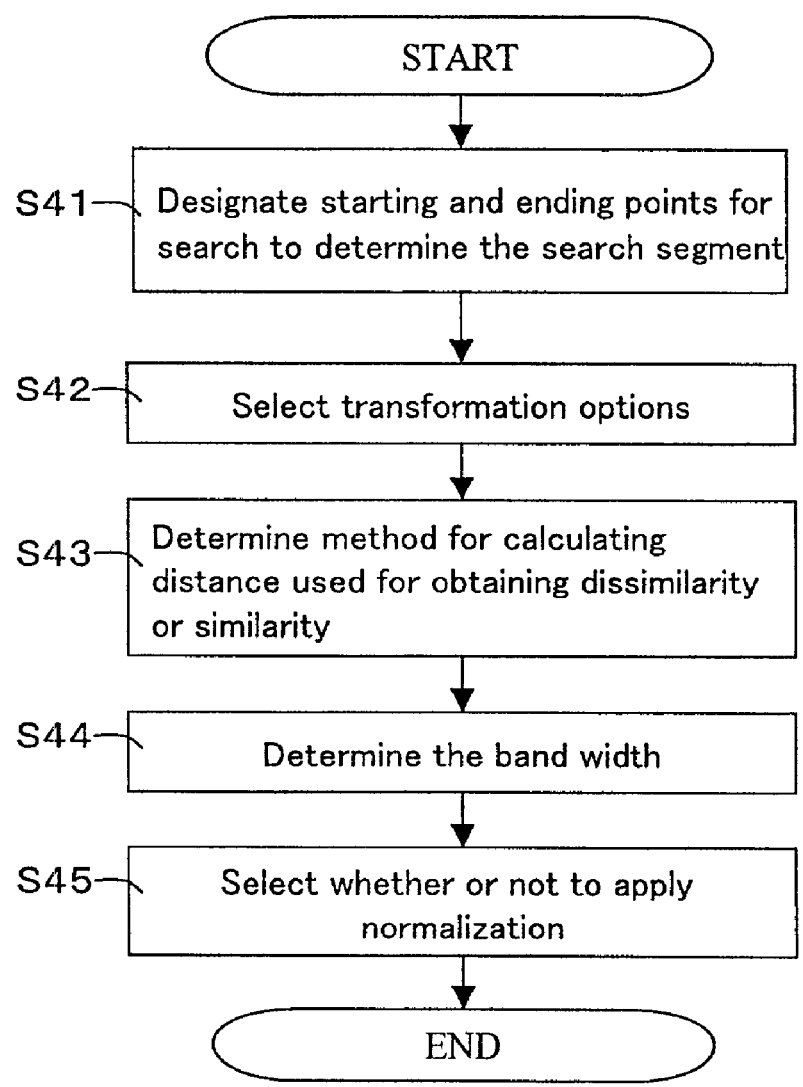
FIG. 11 is a flowchart for illustrating determination of detailed settings of the expression pattern data of the reference gene and selection of a distance calculation.

FIG. 11 is a flowchart for illustrating a detailed process of setting expression pattern data of the reference gene at Step 13 in FIG. 7.

First, a segment of interest is selected by the user using the selected segment frame 30, from the whole expression pattern of the reference gene displayed on the graph display region 29 for reference gene in FIG. 5. The values of the starting and ending points of the selected segment are stored (Step 41).

Figure 12:
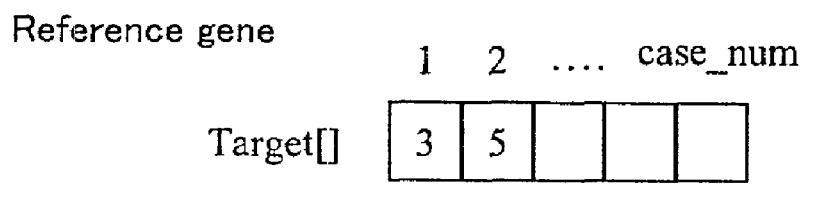

FIG. 12 is a diagram showing a specific structure of the gene expression pattern data corresponding to the search range defined by the selected segment frame 30 shown in FIG. 5. The expression pattern data of the reference gene is indicated as linear array Target[ ]. Specifically, where the expression data of the reference gene is data of gene ID (id) for experiment cases s, s+1, . . . , s+case_num−1, Target[ ] will be Target[1]=Exp[id] [s], . . . , Target[case_num]=Exp[id][s+case_num−1]. Variable case_num indicates the total number of the experiment cases stored in Target[ ].

Then, the expression pattern of the reference gene in the selected segment is transformed depending upon the desired type of relationship between the reference gene and the gene to be extracted from the group of the candidate genes (Step 42). The transformation of the expression pattern is carried out by using the transformation option box 24. Selected transformation formats are checked in the transformation option box 24. The part of the gene expression pattern surrounded by the selected segment frame 30 is transformed according to the selected transformation types and displayed on the respective transformation display windows on the transformation option display region 28 together with a non-transformed curve. Once a transformation format is selected in the transformation option display region 28 by dragging and dropping the format with a pointing device into a slide case 27, the search segment frame 26 is set in the graph display region 25 for the candidate genes. The starting point of search can freely be set by moving the search segment frame 26 to the right or left within the slide case 27.

The transformation options include a "repressed type" where the curve is inverted up-side-down, a "magnification-altered type" where the curve is stretched or shrunk by altering the magnification of expression levels in a direction along the vertical or horizontal axis, and a "user-designated type" where an alternation is made to the expression pattern of the reference gene selected by the user with a pointing device or the like on the transformation option display region. When a similarity search is performed using a transformed pattern of a repressed type, a repressive gene for the reference gene can be found. When a similarity search is performed using a transformed pattern of a magnification-altered type, a gene with amplified expression levels can be found. When a similarity search is performed using a transformed pattern of a user-designated type, a gene search can be conducted reflecting the user's interest or correcting experimental errors. The types of transformation options are not limited to those mentioned above, and appropriate transformation options may further be added to the list.

Figure 22A:
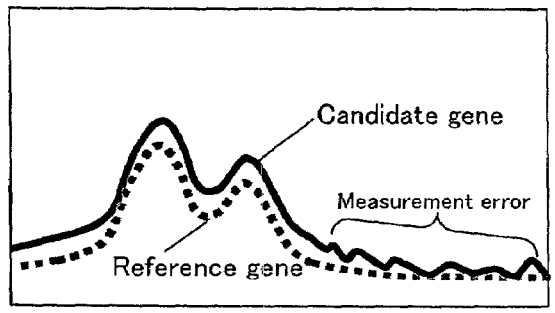
FIGS. 22A to 22F are diagrams showing exemplary gene expression patterns which cannot be detected by a conventional method.
Figure 22B:
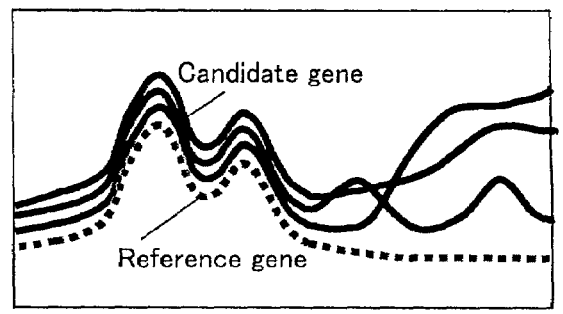
Figure 22C:
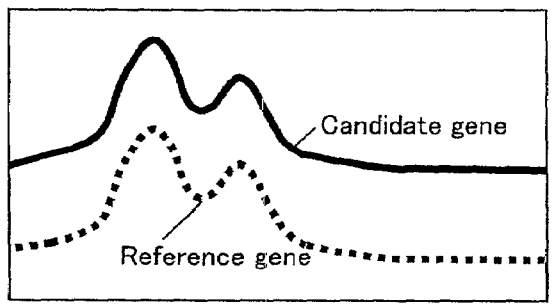
Figure 22D:
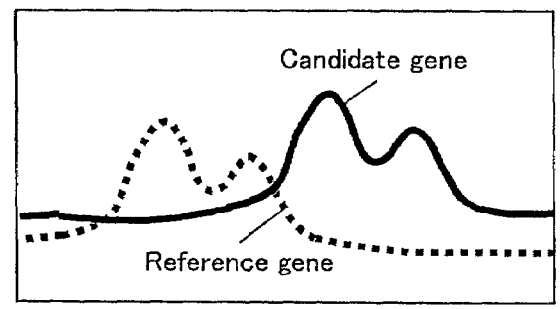
Figure 22E:
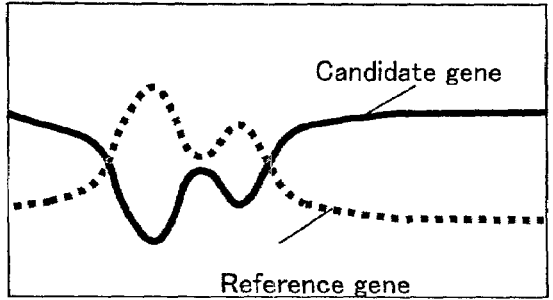
Figure 22F:
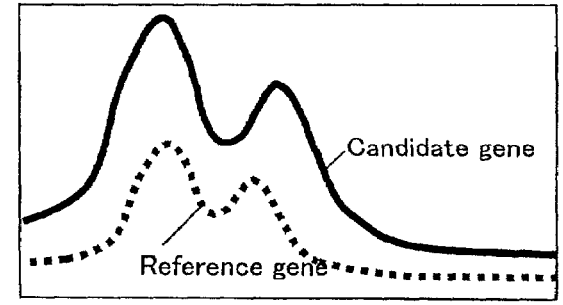
Figure 23:
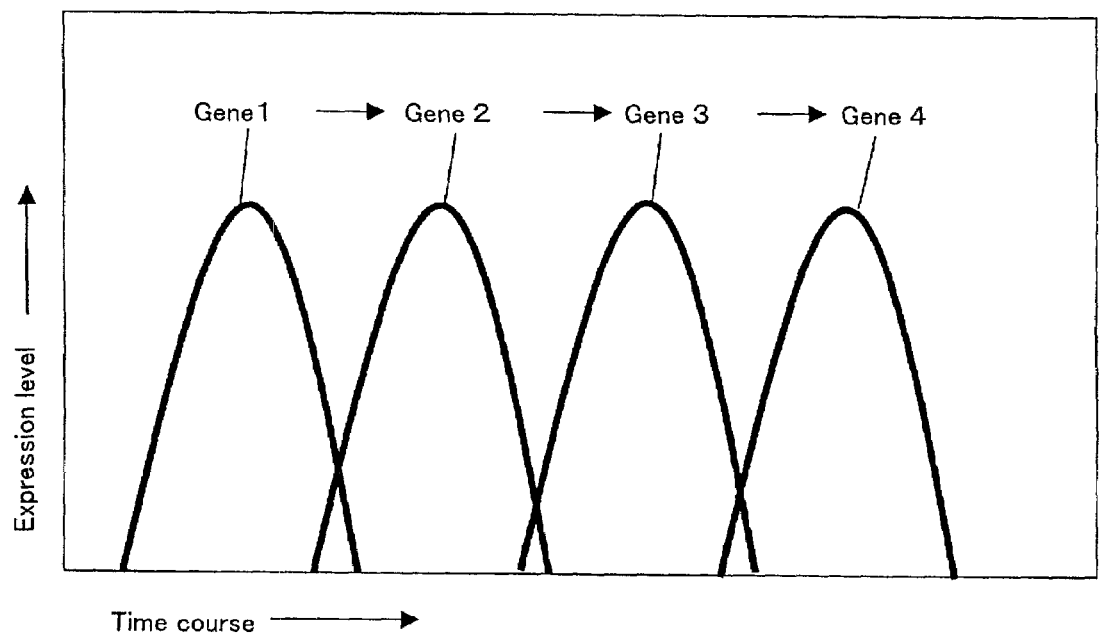
FIG. 23 is a diagram showing an example of gene cascades.
Figure 24A:
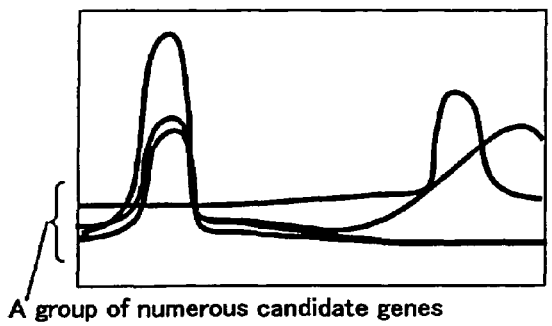
FIGS. 24A to 24D are diagrams for illustrating a conventional method for extracting similar patterns.
Figure 24B:
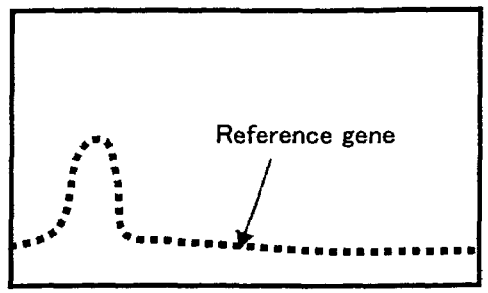
Figure 24C:
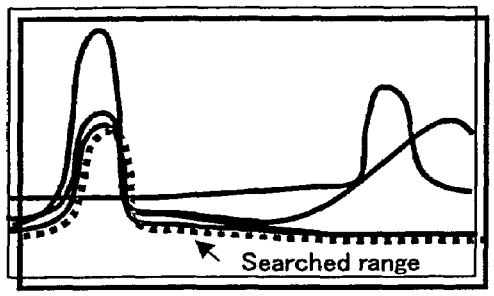
Figure 24D:
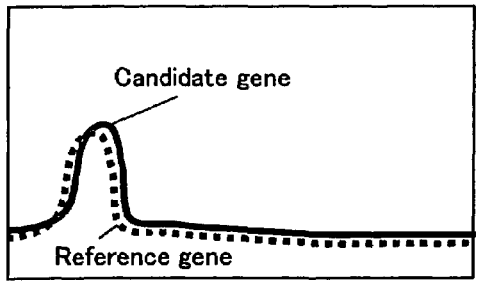

Next, a method for calculating a distance of similarity (dissimilarity) is determined (Step 43). Similarity or dissimilarity is an index for indicating a degree of similarity between two expression patterns. Such index may be a distance where a shorter distance represents higher similarity, or a value such as a correlation coefficient where a higher value represents higher similarity. The former index is referred to as dissimilarity and the latter as similarity. The method for calculating distance for similarity (dissimilarity) is selected in the similarity (dissimilarity) tag 45 shown in FIG. 6D. In the figure, the selectable methods include Pearson's correlation coefficient for similarity, and squared Euclidean distance, standardized squared Euclidean distance, Mahalanobis' (general) distance and Minkowsky distance for dissimilarity. Pearson's correlation coefficient is known to be effective for searching for a gene expression pattern under a fixed magnification as shown in FIG. 22F. When Pearson's correlation coefficient is selected for similarity, the later-described band may automatically be set inaccessible.

Figure 13A:
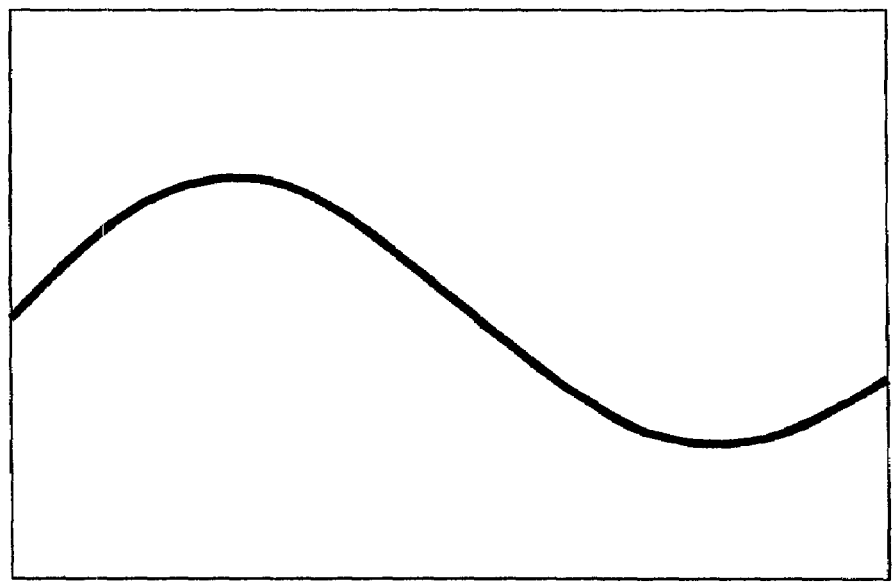
FIGS. 13A and 13B are schematic views for illustrating a band width.
Figure 13B:
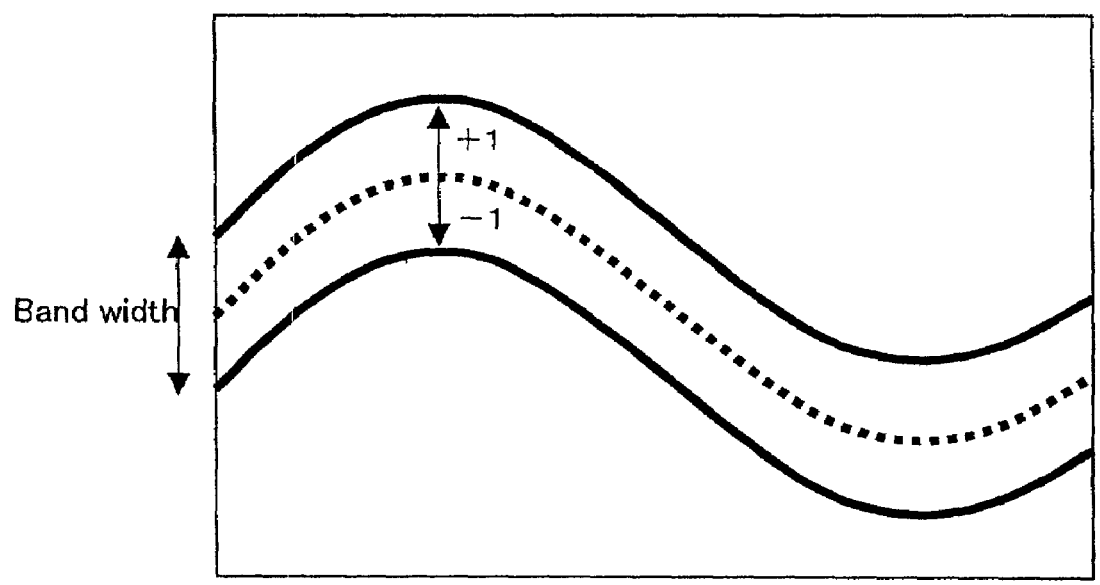

Then, the user is to determine a width of a band by entering a desired value into a band width setting tag 44 shown in FIG. 6C. This value is represented by "W" (Step 44). With reference to FIGS. 13A and 13B, the width of the band will be described. For example, for an expression pattern shown in FIG. 13A, any value ("1" for this example) is added and subtracted to/from the expression levels to form a region having a width in the vertical direction along the expression pattern as shown in FIG. 13B. This region is referred to as the "band". When the width of the band is made narrow, gene expression patterns having a high similarity with the expression pattern of the reference gene in the part defined by the selected segment frame 30 are detected. On the other hand, when the width of the band is made wide, gene expression patterns with relatively low similarity can be detected.

When expression levels of a gene of interest at different parts of body, or before and after drug administration are compared, the obtained gene expression data may not be uniform depending on the difference of experimental environment for each experiment such as difference in temperature or spotting amounts. Briefly, there is a difference in an average value or variance of the expression levels as a whole gene depending on the experiments. Such differences can be corrected by a normalization process. According to the present system, use of the normalization process can be selected (Step 45) by selection in the normalization tag 46 shown in FIG. 6E. When normalization is selected, expression pattern data of both the reference gene and the candidate genes is subjected to a normalization process. Based on the obtained values, the results are displayed on the graph display regions 25 and 29 on the display screen of FIG. 5.

Figure 14:
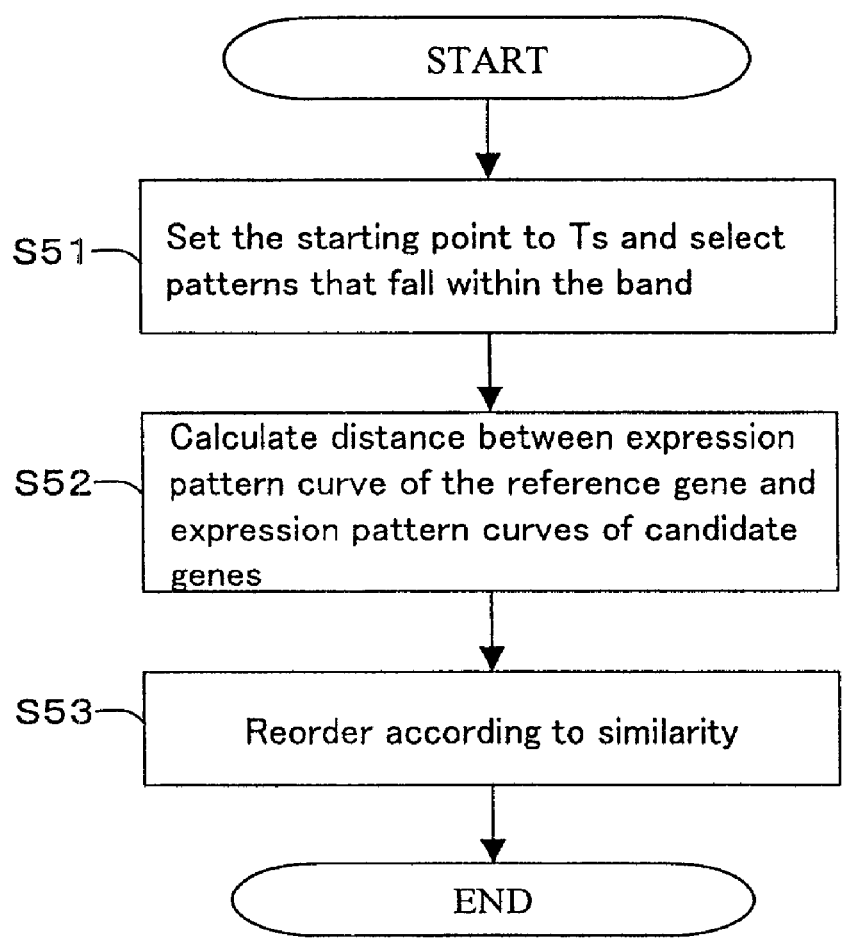
FIG. 14 is a flowchart illustrating detail of extracting similar patterns.

FIG. 14 is a flowchart illustrating detail of extracting similar patterns at Step 16 in FIG. 7. First, the band is used to search for similar expression patterns which fall within the width of the band for the entire segment. Let the starting point on the horizontal axis be Ts (Step 51). When a curve is recognized to have a similar pattern for falling within the band during the search, it can be stored in a memory at that point or after the search has completed.

FIGS. 15A to 15F are diagrams for illustrating exemplary patterns that are recognized or not recognized as similar patterns. Those that are recognized as similar patterns fall within the width of the band for the entire selected segment. Such patterns may be, for example, a pattern that alters in a similar manner to the band as shown in FIG. 15A, a pattern that does not pass the center of the band but entirely overlaps the band as shown in FIGS. 15B and 15C.

Specifically, all of the above cases satisfy the following Expression 1 representing the relationship between expression data Exp[i][Ts], Exp[i][Ts+1], . . . , Exp[i][Ts+case_num−1] (where "i" is the gene ID) and expression pattern data of the reference gene Target[1], Target[2], . . . , Target[case_num]. Gene i that satisfy the relationship of Expression 1 is considered to have a similar expression pattern to that of the reference gene.

$$\text{Target}[1]-W \le \text{Exp}[i][\text{Ts}] \le \text{Target}[1]+W,$$

$$\text{Target}[2]-W \le \text{Exp}[i][\text{Ts}+1] \le \text{Target}[2]+W,$$

$$\text{Target}[\text{case\_num}]-W \le \text{Exp}[i][\text{Ts}+\text{case\_num}] \le \text{Target}[\text{case\_num}]+W, \qquad \text{Expression 1}$$

On the other hand, those that are not recognized as similar patterns are, for example, a pattern which falls within the band from the beginning to the middle but is dislocated from the band at the end as shown in FIG. 15D, a pattern which is dislocated from the band at the beginning as shown in FIG. 15E, and a pattern which falls within the band at the beginning and at the end but is dislocated from the band at the middle as shown in FIG. 15F.

According to the present invention, the band is slid in the vertical direction while the segment is fixed along the horizontal axis as schematically shown in FIGS. 16A to 16D to extract a gene expression pattern that falls within the band. By doing so, a gene expression pattern that changes in a similar manner to the band as shown in FIG. 15A, a gene expression pattern that does not pass the center of the band but entirely overlaps the band as shown in FIGS. 15B and 15C can be recognized.

Figure 16A:
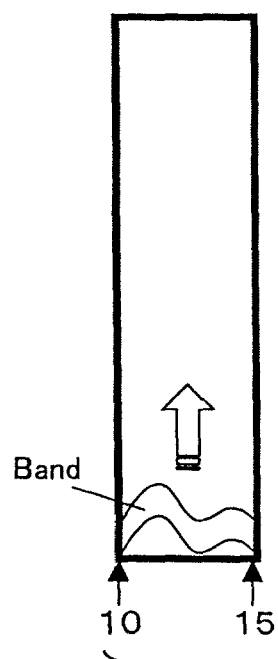
FIGS. 16A to 16D are diagrams for illustrating sliding of a band in a direction along the vertical axis within a selected segment frame.
Figure 16B:
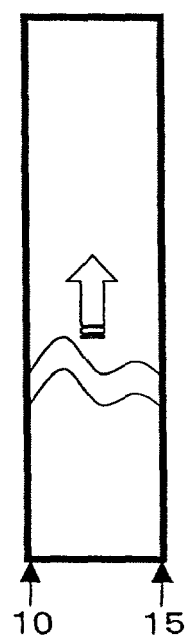
Figure 16C:
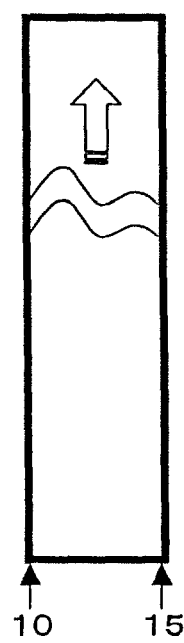
Figure 16D:
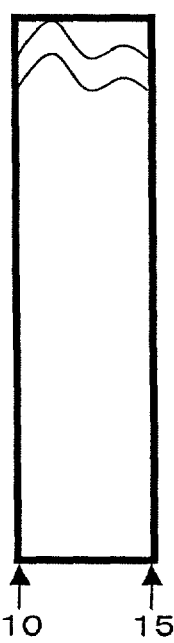
Figure 17A:
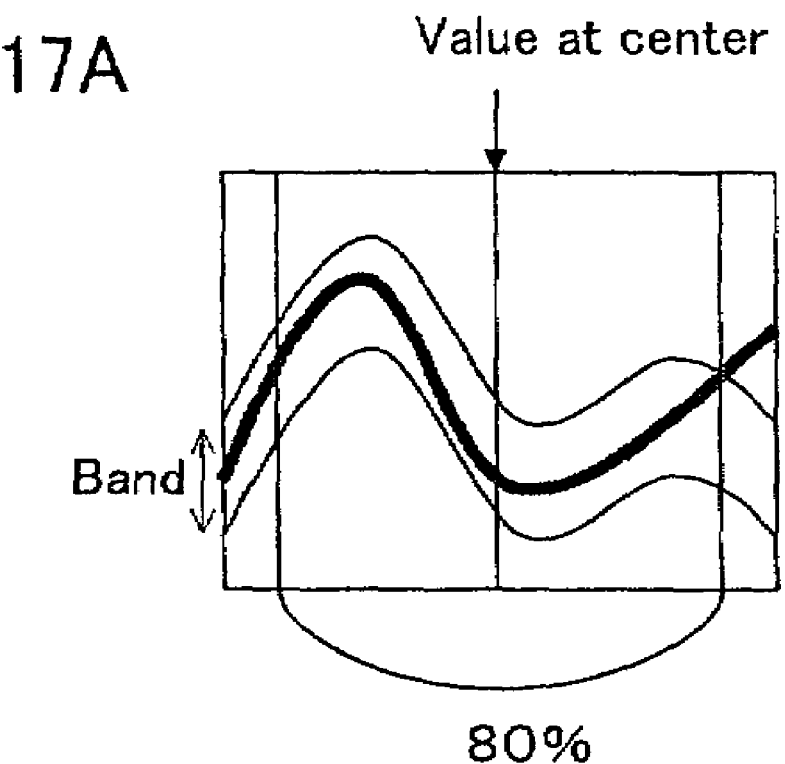
FIGS. 17A and 17B are diagrams showing an exemplary setting of band options.
Figure 17B:
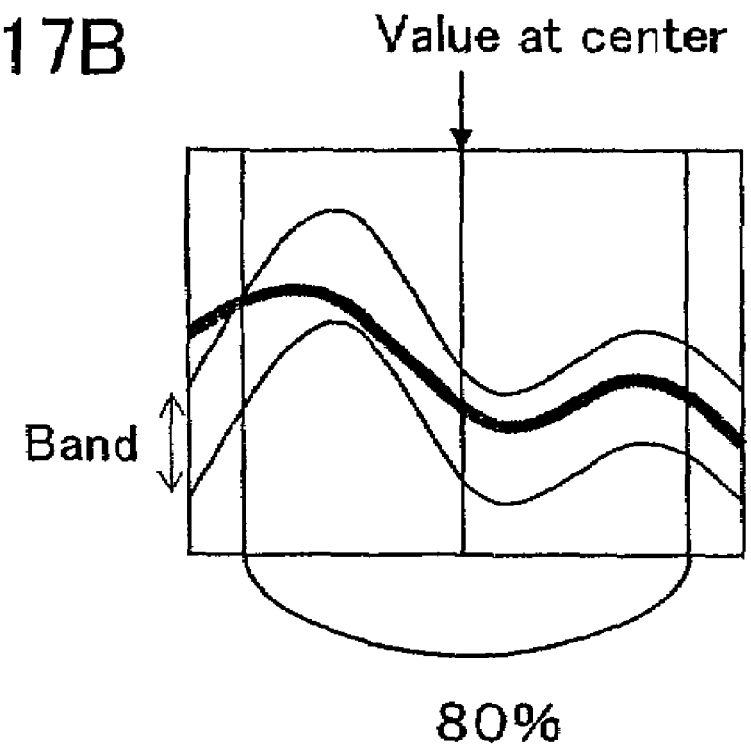

However, the patterns that are not recognized by the above-described technique may include expression patterns having mutual relationship. Therefore, an option is provided where an expression pattern is recognized as a similar pattern if a predetermined range of the middle of the pattern falls within the band even if the beginning and the end of the pattern is dislocated from the band. This option can be set in the band option setting tag 42 shown in FIG. 6A. For example, when the band option is set to "80%", the horizontal width of the selected segment frame 30 is cut down to 80% from both sides. As shown in FIGS. 17A and 17B, the patterns shown in FIGS. 15D and 15E which are not recognized by a search without the band option will be recognized as similar patterns. The pattern shown in FIG. 15F which is dislocated from the band at the middle is not recognized as a similar pattern even with the band option. The search using the band is ended when the band reaches the top of the segment frame as shown in FIG. 16D.

Returning to FIG. 14, similarity (or dissimilarity) of the curves that fall within the band stored in the memory is calculated. Specifically, based on the method for calculating distance selected at Step 43 of FIG. 11, similarity (or dissimilarity) between expression pattern of the reference gene Target[1], Target[2], . . . , Target[case_num] and expression patterns of the candidate genes Exp[i][Ts], Exp[i][Ts+1], . . . , Exp[i][Ts+case_num−1] is calculated (Step 52) (where "i" is the gene ID whose expression pattern falls within the band). Then, the patterns are reordered from higher to lower similarity (or dissimilarity) (Step 53) and the results are displayed on the similarity table 31 on the display screen.

FIG. 18 is a view showing an exemplary display of gene data in the order of similarity. This display appears when the detail button 33 is clicked. A column 62 indicates "similarity", where the value of similarity or dissimilarity calculated by the method selected in similarity (dissimilarity) tag 45 is displayed. A column 63 indicates "search segment", where a curve of candidate data 60 and a curve of reference data 61 within the search segment are displayed. A column 64 indicates "detailed information of gene", where information of the gene is displayed, such as part of body expressed by the gene, nucleotide sequence of the gene, and the like.

While the user can move the search segment frame 26 in the horizontal direction (to the right or left) to determine the starting point of the search on the display screen shown in FIG. 5, search can also be conducted while the starting point of search is automatically transferred within a segment of interest.

FIGS. 19A and 19B are diagrams for illustrating the case where a search is conducted while the starting point of search is automatically transferred. First, as shown in FIG. 19A, the search segment frame 71 on the graph display region 25 for the candidate genes is stretched out toward both sides to cover the segment of interest where the user wants to search. Then, a single transferred distance of the starting point is determined. As a result, the multiple starting points of search at constant intervals can automatically be set along the horizontal axis within the search segment frame 71, for example, as starting points A and B schematically shown in FIG. 19B. Once the up-moving band reaches the top of the search segment frame 71 for each starting point, the band is transferred in the horizontal direction for a predetermined distance, and a search is repeated by moving the band upwards. Accordingly, a search can automatically be conducted for the entire region in the search segment frame 71.

Figure 20A:
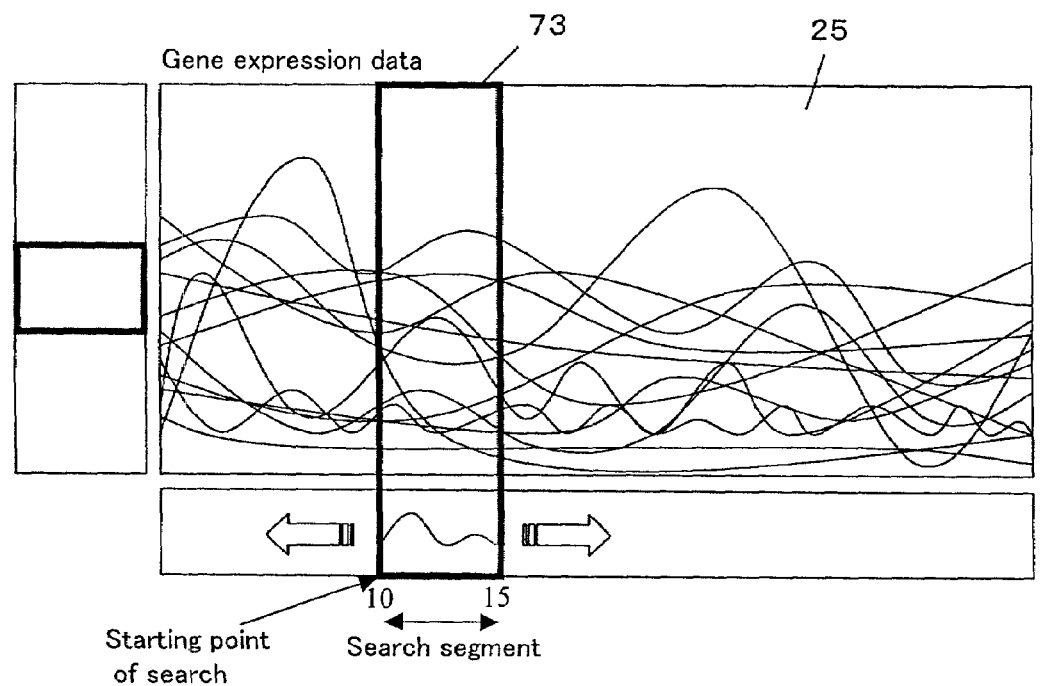
FIGS. 20A and 20B are diagrams for illustrating setting a search segment.
Figure 20B:
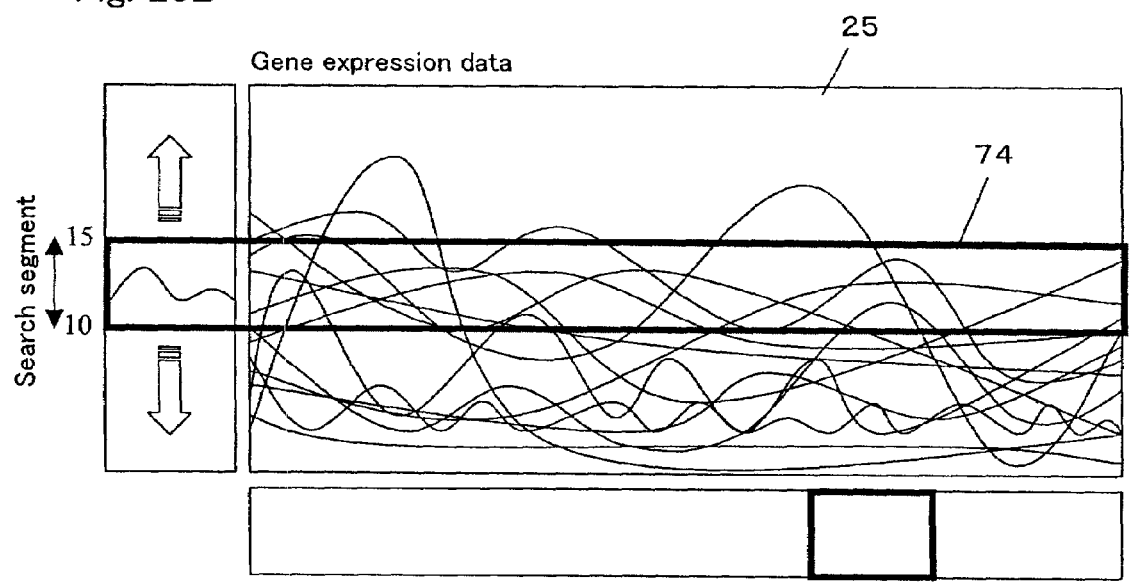

Furthermore, a search can be conducted while sliding the band or the curve in the horizontal direction. FIGS. 20A and 20B are diagrams for illustrating the sliding movement of a band or curve. FIG. 20A illustrates a case where a search segment frame 73 is set longer in the vertical direction. A searching for similar patterns is conducted while moving a band up and down within the search segment frame 73 as described above, the band being a part of an expression pattern of a reference gene or being formed based on an expression pattern of a reference gene. The search segment frame 73 can freely be moved in the horizontal direction as represented by the arrows in the figure.

On the other hand, FIG. 20B illustrates a case where a search segment frame 74 is set longer in the horizontal direction. The search is conducted while sliding a band within the search segment frame 74 in the horizontal direction, the band being a part of an expression pattern of a reference gene or being formed based on an expression pattern of a reference gene. FIGS. 21A to 21D are schematic diagrams for illustrating the search by sliding the band in the horizontal direction. As shown in FIGS. 21A to 21D, the band is slid from left to right with respect to the horizontal axis while the segment is fixed with respect to the expression levels, to extract gene curves that fall within the band. This method is effective for detecting cascades of genes. Again, the search segment frame 74 can freely be moved in the vertical direction as represented by the arrows in FIG. 20B.

The present invention has been described specifically with reference to typical examples. The gene expression database is not limited to a local database, and may be a database on a network. A plurality of transformation options may be selected at the same time for a single reference gene for parallel search. Although only a single gene is selected as a reference gene in the above description, multiple genes may be selected for parallel search for curves similar to respective expression patterns of the genes.

According to the present invention, relative biopolymers can be extracted from a group of numerous unknown biopolymers such as genes, based on expression information of a known biopolymer to efficiently guess the biological functions of the unknown biopolymers.

All publications, patents, and patent applications cited herein are incorporated herein by reference in their entirety.

What is claimed is:

1. A computer-implemented method for analyzing at least one of a plurality of candidate expression wave patterns of biopolymers with respect to a reference expression wave pattern of interest, the method comprising the steps of:
  (a) displaying images of the plurality of candidate expression wave patterns of biopolymers and the reference expression wave pattern of interest on a display unit by assigning expression levels of said biopolymers under an experiment to a first axis and each corresponding one of said biopolymers on a second axis;
  (b) selecting a section of the reference expression wave pattern;
  (c) extending a pattern shape of the selected section a predetermined amount up and down equally into a band-shape wave pattern having a constant width thereof in the direction parallel with the first axis by adding to and subtracting from said pattern shape of the selected section said predetermined amount of expression levels;
  (d) searching each of the plurality of candidate expression wave patterns for at least one section therein with a pattern shape containing a portion falling within the band-shape wave pattern and satisfying a predetermined value of similarity with the band-shape wave pattern by moving and displaying an image of the band-shape wave pattern along each of the images of the plurality of candidate expression wave patterns of biopolymers and visually overlaying the band-shape wave pattern on said candidate expression wave patterns, wherein said portion is defined by setting a percentage of a horizontal width of said at least one section of the plurality of candidate expression wave patterns at less than 50% and more than 0% so as to cut off equally from two ends of said at least one section of the plurality of candidate expression wave patterns and then to determine whether said portion falls within the band-shape wave pattern, and a similarity of said portion with the band-shape wave pattern being calculated by a selected method if said portion falls within the band-shape wave pattern;
  (e) extracting expression wave pattern data of each searched section; and
  (f) displaying the selected section overlappingly with said extracted expression wave patterns and in conjunction with information of said biopolymers and said similarity thereby discovering at least one new fact of said biopolymers,
  wherein the biopolymers consist of genes, DNAs, or DNA fragments.

2. A computer-implemented method for analyzing at least one of a plurality of candidate expression wave patterns of biopolymers with respect to a reference expression wave pattern of interest, the method comprising the steps of:
  (a) displaying images of the plurality of candidate expression wave patterns of biopolymers and the reference expression wave pattern of interest on a display unit by assigning expression levels of said biopolymers under an experiment to a first axis and corresponding points in time for measuring said expression levels on a second axis;
  (b) selecting a section of the reference expression wave pattern;
  (c) extending a pattern shape of the selected section a predetermined amount up and down equally into a band-shape wave pattern having a constant width thereof in the direction parallel with the first axis by adding to and subtracting from said pattern shape of the selected section said predetermined amount of expression levels;

(d) searching each of the plurality of candidate expression wave patterns for at least one section therein with a pattern shape containing a portion falling within the band-shape wave pattern and satisfying a predetermined value of similarity with the band-shape wave pattern by moving and displaying an image of the band-shape wave pattern along each of the images of the plurality of candidate expression wave patterns of biopolymers and visually overlaying the band-shape wave pattern on said candidate expression wave patterns, wherein said portion is defined by setting a percentage of a horizontal width of said at least one section of the plurality of candidate expression wave patterns at less than 50% and more than 0% so as to cut off equally from two ends of said at least one section of the plurality of candidate expression wave patterns and then to determine whether said portion falls within the band-shape wave pattern, and a similarity of said portion with the band-shape wave pattern being calculated by a selected method if said portion falls within the band-shape wave pattern;

(e) extracting expression wave pattern data of each searched section; and (f) displaying the selected section overlappingly with said extracted expression wave patterns and in conjunction with information of said biopolymers and said similarity thereby discovering at least one new fact of said biopolymers wherein the biopolymers consist of genes, DNAs, or DNA fragments.

3. A computer-implemented method for analyzing at least one of a plurality of candidate expression wave patterns of biopolymers with respect to a reference expression wave pattern of interest, the method comprising the steps of:

(a) displaying images of the plurality of candidate expression wave patterns of biopolymers and the reference expression wave pattern of interest on a display unit by assigning expression levels of said biopolymers of different species under an experiment to a first axis and each corresponding one of said species on a second axis;

(b) selecting a section of the reference expression wave pattern;

(c) extending a pattern shape of the selected section a predetermined amount up and down equally into a band-shape wave pattern having a constant width thereof in the direction parallel with the first axis by adding to and subtracting from said pattern shape of the selected section said predetermined amount of expression levels;

(d) searching each of the plurality of candidate expression wave patterns for at least one section therein with a pattern shape containing a portion falling within the band-shape wave pattern and satisfying a predetermined value of similarity with the band-shape wave pattern by moving and displaying an image of the band-shape wave pattern along each of the images of the plurality of candidate expression wave patterns of biopolymers and visually overlaying the band-shape wave pattern on said candidate expression wave patterns, wherein said portion is defined by setting a percentage of a horizontal width of said at least one section of the plurality of candidate expression wave patterns at less than 50% and more than 0% so as to cut off equally from two ends of said at least one section of the plurality of candidate expression wave patterns and then to determine whether said portion falls within the band-shape wave pattern, and a similarity of said portion with the band-shape wave pattern being calculated by a selected method if said portion falls within the band-shape wave pattern;

(e) extracting expression wave pattern data of each searched section; and (f) displaying the selected section overlappingly with said extracted expression wave patterns and in conjunction with information of said biopolymers and said similarity thereby discovering at least one new fact of said biopolymers wherein the biopolymers consist of genes, DNAs, or DNA fragments.

4. A computer-implemented method for analyzing at least one of a plurality of candidate expression wave patterns of biopolymers with respect to a reference expression wave pattern of interest, the method comprising the steps of:

(a) displaying images of the plurality of candidate expression wave patterns of biopolymers and the reference expression wave pattern of interest on a display unit by assigning expression levels of said biopolymers of different parts of an organism body under an experiment to a first axis and each corresponding one of said parts of the organism body on a second axis;

(b) selecting a section of the reference expression wave pattern;

(c) extending a pattern shape of the selected section a predetermined amount up and down equally into a band-shape wave pattern having a constant width thereof in the direction parallel with the first axis by adding to and subtracting from said pattern shape of the selected section said predetermined amount of expression levels;

(d) searching each of the plurality of candidate expression wave patterns for at least one section therein with a pattern shape containing a portion falling within the band-shape wave pattern and satisfying a predetermined value of similarity with the band-shape wave pattern by moving and displaying an image of the band-shape wave pattern along each of the images of the plurality of candidate expression wave patterns of biopolymers and visually overlaying the band-shape wave pattern on said candidate expression wave patterns, wherein said portion is defined by setting a percentage of a horizontal width of said at least one section of the plurality of candidate expression wave patterns at less than 50% and more than 0% so as to cut off equally from two ends of said at least one section of the plurality of candidate expression wave patterns and then to determine whether said portion falls within the band-shape wave pattern, and a similarity of said portion with the band-shape wave pattern being calculated by a selected method if said portion falls within the band-shape wave pattern;

(e) extracting expression wave pattern data of each searched section; and (f) displaying the selected section overlappingly with said extracted expression wave patterns and in conjunction with information of said biopolymers and said similarity thereby discovering at least one new fact of said biopolymers wherein the biopolymers consist of genes, DNAs, or DNA fragments.

5. A computer-implemented method for analyzing at least one of a plurality of candidate expression wave patterns of biopolymers with respect to a reference expression wave pattern of interest, the method comprising the steps of:

(a) displaying images of the plurality of candidate expression wave patterns of biopolymers and the reference expression wave pattern of interest on a display unit by assigning expression levels of said biopolymers under experiments presence or absence of artificial conditions to a first axis and each corresponding one of said experiments presence or absence of said artificial conditions on a second axis;

(b) selecting a section of the reference expression wave pattern;

(c) extending a pattern shape of the selected section a predetermined amount up and down equally into a band-shape wave pattern having a constant width thereof in the direction parallel with the first axis by adding to and subtracting from said pattern shape of the selected section said predetermined amount of expression levels;

(d) searching each of the plurality of candidate expression wave patterns for at least one section therein with a pattern shape containing a portion falling within the band-shape wave pattern and satisfying a predetermined value of similarity with the band-shape wave pattern by moving and displaying an image of the band-shape wave pattern along each of the images of the plurality of candidate expression wave patterns of biopolymers and visually overlaying the band-shape wave pattern on said candidate expression wave patterns, wherein said portion is defined by setting a percentage of a horizontal width of said at least one section of the plurality of candidate expression wave patterns at less than 50% and more than 0% so as to cut off equally from two ends of said at least one section of the plurality of candidate expression wave patterns and then to determine whether said portion falls within the band-shape wave pattern, and a similarity of said portion with the band-shape wave pattern being calculated by a selected method if said portion falls within the band-shape wave pattern;

(e) extracting expression wave pattern data of each searched section; and (f) displaying the selected section overlappingly with said extracted expression wave patterns and in conjunction with information of said biopolymers and said similarity thereby discovering at least one new fact of said biopolymers wherein the biopolymers consist of genes, DNAs, or DNA fragments.

6. A computer-implemented method for analyzing at least one of a plurality of candidate expression wave patterns of biopolymers with respect to a reference expression wave pattern of interest, the method comprising the steps of:

(a) displaying images of the plurality of candidate expression wave patterns of biopolymers and the reference expression wave pattern of interest on a display unit by assigning expression levels of said biopolymers under experiments to a first axis and each corresponding one of said experiments on said biopolymers on a second axis;

(b) selecting a section of the reference expression wave pattern;

(c) extending a pattern shape of the selected section a predetermined amount up and down equally into a band-shape wave pattern having a constant width thereof in the direction parallel with the first axis by adding to and subtracting from said pattern shape of the selected section said predetermined amount of expression levels;

(d) searching each of the plurality of candidate expression wave patterns for at least one section therein with a pattern shape containing a portion falling within the band-shape wave pattern and satisfying a predetermined value of similarity with the band-shape wave pattern by moving and displaying an image of the band-shape wave pattern along each of the images of the plurality of candidate expression wave patterns of biopolymers and visually overlaying the band-shape wave pattern on said candidate expression wave patterns, wherein said portion is defined by setting a percentage of a horizontal width of said at least one section of the plurality of candidate expression wave patterns at less than 50% and more than 0% so as to cut off equally from two ends of said at least one section of the plurality of candidate expression wave patterns and then to determine whether said portion falls within the band-shape wave pattern, and a similarity of said portion with the band-shape wave pattern being calculated by a selected method if said portion falls within the band-shape wave pattern;

(e) extracting expression wave pattern data of each searched section; and (f) displaying the selected section overlappingly with said extracted expression wave patterns and in conjunction with information of said biopolymers and said similarity thereby discovering at least one new fact of said biopolymers, wherein the biopolymers consist of genes, DNAs, or DNA fragments and wherein the experiments are experiments involving at least one of different species, different parts of an organism body, and the presence or absence of artificial conditions.

7. A computer-implemented method for analyzing at least one of a plurality of candidate expression wave patterns of candidate biopolymers with respect to a reference expression wave pattern of interest, the method comprising the steps of:

(a) displaying images of the plurality of candidate expression wave patterns of candidate biopolymers and the reference expression wave pattern of interest on a display unit by assigning expression levels of said biopolymers under an experiment to a first axis and each corresponding one of said biopolymers on a second axis;

(b) selecting a section of the reference expression wave pattern of a reference biopolymer;

(c) extending a pattern shape of the selected section a predetermined amount up and down equally into a band-shape wave pattern having a constant width thereof in the direction parallel with the first axis by adding to and subtracting from said pattern shape of the selected section said predetermined amount of expression levels;

(d) comparing each section of the plurality of candidate expression wave patterns of candidate biopolymers for at least one section therein with a pattern shape containing a portion falling within the band-shape wave pattern and satisfying a predetermined value of similarity with the band-shape wave pattern by moving and displaying an image of the band-shape wave pattern along each of the images of the plurality of candidate expression wave patterns of candidate biopolymers and visually overlaying the band-shape wave pattern on said candidate expression wave patterns, wherein said portion is defined by setting a percentage of a horizontal width of said at least one section of the plurality of candidate expression wave patterns at less than 50% and more than 0% so as to cut off equally from two ends of said at least one section of the plurality of candidate expression wave patterns and then to determine whether said portion falls within the band-shape wave pattern, and a similarity of said portion with the band-shape wave pattern being calculated by a selected method if said portion falls within the band-shape wave pattern;

(e) extracting expression wave pattern data of each compared section; and (f) displaying the selected section overlappingly with said extracted expression wave patterns and in conjunction with information of said biopolymers and said similarity thereby discovering at least one new fact of said biopolymers, wherein the biopolymers consist of genes, DNAs, or DNA fragments.

8. A computer-implemented method for analyzing at least one of a plurality of candidate expression wave patterns of candidate biopolymers with respect to a reference expression wave pattern of interest, the method comprising the steps of:

(a) displaying images of the plurality of candidate expression wave patterns of candidate biopolymers and the reference expression wave pattern of interest on a display unit by assigning expression levels of said biopolymers under an experiment to a first axis and corresponding points in time for measuring said expression levels on a second axis;

(b) selecting a section of the reference expression wave pattern of a reference biopolymer;

(c) extending a pattern shape of the selected section a predetermined amount up and down equally into a band-shape wave pattern having a constant width thereof in the direction parallel with the first axis by adding to and subtracting from said pattern shape of the selected section said predetermined amount of expression levels;

(d) comparing each section of the plurality of candidate expression wave patterns of candidate biopolymers for at least one section therein with a pattern shape containing a portion falling within the band-shape wave pattern and satisfying a predetermined value of similarity with the band-shape wave pattern by moving and displaying an image of the band-shape wave pattern along each of the images of the plurality of candidate expression wave patterns of candidate biopolymers and visually overlaying the band-shape wave pattern on said candidate expression wave patterns, wherein said portion is defined by setting a percentage of a horizontal width of said at least one section of the plurality of candidate expression wave patterns at less than 50% and more than 0% so as to cut off equally from two ends of said at least one section of the plurality of candidate expression wave patterns and then to determine whether said portion falls within the band-shape wave pattern, and a similarity of said portion with the band-shape wave pattern being calculated by a selected method if said portion falls within the band-shape wave pattern;

(e) extracting expression wave pattern data of each compared section; and (f) displaying the selected section overlappingly with said extracted expression wave patterns and in conjunction with information of said biopolymers and said similarity thereby discovering at least one new fact of said biopolymers wherein the biopolymers consist of genes, DNAs, or DNA fragments.

9. A computer-implemented method for analyzing at least one of a plurality of candidate expression wave patterns of candidate biopolymers with respect to a reference expression wave pattern of interest, the method comprising the steps of:

(a) displaying images of the plurality of candidate expression wave patterns of candidate biopolymers and the reference expression wave pattern of interest on a display unit by assigning expression levels of said biopolymers of different species under an experiment to a first axis and each corresponding one of said species on a second axis;

(b) selecting a section of the reference expression wave pattern of a reference biopolymer;

(c) extending a pattern shape of the selected section a predetermined amount up and down equally into a band-shape wave pattern having a constant width thereof in the direction parallel with the first axis by adding to and subtracting from said pattern shape of the selected section said predetermined amount of expression levels;

(d) comparing each section of the plurality of candidate expression wave patterns of candidate biopolymers for at least one section therein with a pattern shape containing a portion falling within the band-shape wave pattern and satisfying a predetermined value of similarity with the band-shape wave pattern by moving and displaying an image of the band-shape wave pattern along each of the images of the plurality of candidate expression wave patterns of candidate biopolymers and visually overlaying the band-shape wave pattern on said candidate expression wave patterns, wherein said portion is defined by setting a percentage of a horizontal width of said at least one section of the plurality of candidate expression wave patterns at less than 50% and more than 0% so as to cut off equally from two ends of said at least one section of the plurality of candidate expression wave patterns and then to determine whether said portion falls within the band-shape wave pattern, and a similarity of said portion with the band-shape wave pattern being calculated by a selected method if said portion falls within the band-shape wave pattern;

(e) extracting expression wave pattern data of each compared section; and (f) displaying the selected section overlapping with said extracted expression wave patterns and in conjunction with information of said biopolymers and said similarity thereby discovering at least one new fact of said biopolymers wherein the biopolymers consist of genes, DNAs, or DNA fragments.

10. A computer-implemented method for analyzing at least one of a plurality of candidate expression wave patterns of candidate biopolymers with respect to a reference expression wave pattern of interest, the method comprising the steps of:

(a) displaying images of the plurality of candidate expression wave patterns of candidate biopolymers and the reference expression wave pattern of interest on a display unit by assigning expression levels of said biopolymers of different parts of an organism body under an experiment to a first axis and each corresponding one of said parts of the organism body on a second axis;

(b) selecting a section of the reference expression wave pattern of a reference biopolymer;
(c) extending a pattern shape of the selected section a predetermined amount up and down equally into a band-shape wave pattern having a constant width thereof in the direction parallel with the first axis by adding to and subtracting from said pattern shape of the selected section said predetermined amount of expression levels;
(d) comparing each section of the plurality of candidate expression wave patterns of candidate biopolymers for at least one section therein with a pattern shape containing a portion falling within the band-shape wave pattern and satisfying a predetermined value of similarity with the band-shape wave pattern by moving and displaying an image of the band-shape wave pattern along each of the images of the plurality of candidate expression wave patterns of candidate biopolymers and visually overlaying the band-shape wave pattern on said candidate expression wave patterns, wherein said portion is defined by setting a percentage of a horizontal width of said at least one section of the plurality of candidate expression wave patterns at less than 50% and more than 0% so as to cut off equally from two ends of said at least one section of the plurality of candidate expression wave patterns and then to determine whether said portion falls within the band-shape wave pattern, and a similarity of said portion with the band-shape wave pattern being calculated by a selected method if said portion falls within the band-shape wave pattern;
(e) extracting expression wave pattern data of each compared section; and
(f) displaying the selected section overlappingly with said extracted expression wave patterns and in conjunction with information of said biopolymers and said similarity thereby discovering at least one new fact of said biopolymers wherein the biopolymers consist of genes, DNAs, or DNA fragments.

11. A computer-implemented method for analyzing at least one of a plurality of candidate expression wave patterns of candidate biopolymers with respect to a reference expression wave pattern of interest, the method comprising the steps of:
(a) displaying images of the plurality of candidate expression wave patterns of candidate biopolymers and the reference expression wave pattern of interest on a display unit by assigning expression levels of said biopolymers under experiments presence or absence of artificial conditions to a first axis and each corresponding one of said experiments presence or absence of said artificial conditions on a second axis;
(b) selecting a section of the reference expression wave pattern of a reference biopolymer;
(c) extending a pattern shape of the selected section a predetermined amount up and down equally into a band-shape wave pattern having a constant width thereof in the direction parallel with the first axis by adding to and subtracting from said pattern shape of the selected section said predetermined amount of expression levels;
(d) comparing each section of the plurality of candidate expression wave patterns of candidate biopolymers for at least one section therein with a pattern shape containing a portion falling within the band-shape wave pattern and satisfying a predetermined value of similarity with the band-shape wave pattern by moving and displaying an image of the band-shape wave pattern along each of the images of the plurality of candidate expression wave patterns of candidate biopolymers and visually overlaying the band-shape wave pattern on said candidate expression wave patterns, wherein said portion is defined by setting a percentage of a horizontal width of said at least one section of the plurality of candidate expression wave patterns at less than 50% and more than 0% so as to cut off equally from two ends of said at least one section of the plurality of candidate expression wave patterns and then to determine whether said portion falls within the band-shape wave pattern, and a similarity of said portion with the band-shape wave pattern being calculated by a selected method if said portion falls within the band-shape wave pattern;
(e) extracting expression wave pattern data of each compared section; and
(f) displaying the selected section overlappingly with said extracted expression wave patterns and in conjunction with information of said biopolymers and said similarity thereby discovering at least one new fact of said biopolymers wherein the biopolymers consist of genes, DNAs, or DNA fragments.

12. A computer-implemented method for analyzing at least one of a plurality of candidate expression wave patterns of candidate biopolymers with respect to a reference expression wave pattern of interest, the method comprising the steps of:
(a) displaying images of the plurality of candidate expression wave patterns of candidate biopolymers and the reference expression wave pattern of interest on a display unit by assigning expression levels of said biopolymers under experiments to a first axis and each corresponding one of said experiments on said biopolymers on a second axis;
(b) selecting a section of the reference expression wave pattern of a reference biopolymer;
(c) extending a pattern shape of the selected section a predetermined amount up and down equally into a band-shape wave pattern having a constant width thereof in the direction parallel with the first axis by adding to and subtracting from said pattern shape of the selected section said predetermined amount of expression levels;
(d) comparing each section of the plurality of candidate expression wave patterns of candidate biopolymers for at least one section therein with a pattern shape containing a portion falling within the band-shape wave pattern and satisfying a predetermined value of similarity with the band-shape wave pattern by moving and displaying an image of the band-shape wave pattern along each of the images of the plurality of candidate expression wave patterns of candidate biopolymers and visually overlaying the band-shape wave pattern on said candidate expression wave patterns, wherein said portion is defined by setting a percentage of a horizontal width of said at least one section of the plurality of candidate expression wave patterns at less than 50% and more than 0% so as to cut off equally from two ends of said at least one section of the plurality of candidate expression wave patterns and then to determine whether said portion falls within the band-shape wave pattern, and a similarity of said portion with the band-shape wave pattern being calculated by a selected method if said portion falls within the band-shape wave pattern;

(e) extracting expression wave pattern data of each compared section; and
(f) displaying the selected section overlappingly with said extracted expression wave patterns and in conjunction with information of said biopolymers and said similarity thereby discovering at least one new fact of said biopolymers, wherein the biopolymers consist of genes, DNAs, or DNA fragments and
wherein the experiments are experiments involving at least one of different species, different parts of an organism body, and the presence or absence of artificial conditions.

13. A computer-implemented method for analyzing at least one of a plurality of candidate expression wave patterns of biopolymers with respect to a reference expression wave pattern of interest, the method comprising the steps of:
(a) displaying images of the plurality of candidate expression wave patterns of biopolymers and the reference expression wave pattern of interest on a display unit by assigning expression levels of said biopolymers under experiments to a first axis and each corresponding one of said experiments on said biopolymers on a second axis;
(b) selecting a section of the reference expression wave pattern;
(c) extending a pattern shape of the selected section a predetermined amount up and down equally into a band-shape wave pattern having a constant width thereof in the direction parallel with the first axis by adding to and subtracting from said pattern shape of the selected section said predetermined amount of expression levels;
(d) searching each of the plurality of candidate expression wave patterns for at least one section therein with a pattern shape containing a portion falling within the band-shape wave pattern and satisfying a predetermined value of similarity with the band-shape wave pattern by moving and displaying an image of the band-shape wave pattern along each of the images of the plurality of candidate expression wave patterns of candidate biopolymers and visually overlaying the band-shape wave pattern on said candidate expression wave patterns, wherein said portion is defined by setting a percentage of a horizontal width of said at least one section of the plurality of candidate expression wave patterns at less than 50% and more than 0% so as to cut off equally from two ends of said at least one section of the plurality of candidate expression wave patterns and then to determine whether said portion falls within the band-shape wave pattern, and a similarity of said portion with the band-shape wave pattern being calculated by a selected method if said portion falls within the band-shape wave pattern;
(e) extracting expression wave pattern data of each searched section;
(f) ranking candidate expression wave patterns containing said section with a pattern shape satisfying the degree of similarity with the pattern shape of the selected section based upon an order of similarity to which each candidate expression wave pattern satisfies the degree of similarity; and
(g) displaying the selected section overlappingly with said extracted expression wave patterns and in conjunction with information of said biopolymers in the order of similarity thereby discovering at least one new fact of said biopolymers, wherein the biopolymers consist of genes, DNAs, or DNA fragments and
wherein the order of similarity is judged by how closely the pattern shape of a section of a candidate expression wave pattern matches with the selected section of the reference expression wave pattern.

14. A computer-implemented method for analyzing at least one of a plurality of candidate expression wave patterns of candidate biopolymers with respect to a reference expression wave pattern of interest, the method comprising the steps of:
(a) displaying images of the plurality of candidate expression wave patterns of candidate biopolymers and the reference expression wave pattern of interest on a display unit by assigning expression levels of said biopolymers under experiments to a first axis and each corresponding one of said experiments on said biopolymers on a second axis;
(b) selecting a section of the reference expression wave pattern of a reference biopolymer;
(c) extending a pattern shape of the selected section a predetermined amount up and down equally into a band-shape wave pattern having a constant width thereof in the direction parallel with the first axis by adding to and subtracting from said pattern shape of the selected section said predetermined amount of expression levels;
(d) comparing each section of the plurality of candidate expression wave patterns of candidate biopolymers for at least one section therein with a pattern shape containing a portion falling within the band-shape wave pattern and satisfying a predetermined value of similarity with the band-shape wave pattern by moving and displaying an image of the band-shape wave pattern along each of the images of the plurality of candidate expression wave patterns of candidate biopolymers and visually overlaying the band-shape wave pattern on said candidate expression wave patterns, wherein said portion is defined by setting a percentage of a horizontal width of said at least one section of the plurality of candidate expression wave patterns at less than 50% and more than 0% so as to cut off equally from two ends of said at least one section of the plurality of candidate expression wave patterns and then to determine whether said portion falls within the band-shape wave pattern, and a similarity of said portion with the band-shape wave pattern being calculated by a selected method if said portion falls within the band-shape wave pattern;
(e) extracting expression wave pattern data of each compared section;
(f) ranking candidate expression wave patterns containing said section with a pattern shape satisfying the degree of similarity with the pattern shape of the selected section based upon an order of similarity to which each candidate expression wave pattern satisfies the degree of similarity; and
(g) displaying the selected section overlappingly with said extracted expression wave patterns and in conjunction with information of said biopolymers in the order of similarity thereby discovering at least one new fact of said biopolymers, wherein the biopolymers consist of genes, DNAs, or DNA fragments and
wherein the order of similarity is judged by how closely the pattern shape of a section of a candidate expression wave pattern matches with the selected section of the reference expression wave pattern.

* * * * *